US008019161B2

(12) United States Patent
Morokuma et al.

(10) Patent No.: US 8,019,161 B2
(45) Date of Patent: Sep. 13, 2011

(54) METHOD, DEVICE AND COMPUTER PROGRAM OF LENGTH MEASUREMENT

(75) Inventors: Hidetoshi Morokuma, Hitachinaka (JP);
Takumichi Sutani, Hitachinaka (JP);
Ryoichi Matsuoka, Hitachinaka (JP);
Hitoshi Komuro, Hitachinaka (JP);
Akiyuki Sugiyama, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 1184 days.

(21) Appl. No.: 11/717,772

(22) Filed: Mar. 14, 2007

(65) Prior Publication Data

US 2007/0221842 A1 Sep. 27, 2007

(30) Foreign Application Priority Data

Mar. 14, 2006 (JP) .................................. 2006-068480

(51) Int. Cl.
*G06K 9/46* (2006.01)
(52) U.S. Cl. ........................................................ 382/190
(58) Field of Classification Search .................... None
See application file for complete search history.

(56) References Cited

U.S. PATENT DOCUMENTS

| 5,962,173 | A | * | 10/1999 | Leroux et al. ...................... 430/5 |
| 6,657,735 | B2 | | 12/2003 | Noda et al. |
| 6,868,175 | B1 | | 3/2005 | Yamamoto et al. |
| 7,151,855 | B2 | | 12/2006 | Mitsui |
| 7,544,446 | B2 | * | 6/2009 | Lee ..................................... 430/5 |
| 2005/0086618 | A1 | | 4/2005 | Ito et al. |

FOREIGN PATENT DOCUMENTS

| CN | 1205545 A | 1/1999 |
| CN | 1497695 A | 5/2004 |
| EP | 0 890 983 A1 | 1/1999 |
| JP | 2001-338304 | 12/2001 |
| JP | 2002-93875 | 3/2002 |
| JP | 2005-98885 | 4/2005 |

OTHER PUBLICATIONS

Japanese Office Action, w/ partial English translation thereof, issued in Japanese Patent Application No. JP 2006-068480 dated Nov. 16, 2010.

* cited by examiner

*Primary Examiner* — Daniel G Mariam
*Assistant Examiner* — Elisa M Rice
(74) *Attorney, Agent, or Firm* — McDermott Will & Emery LLP

(57) ABSTRACT

A workpiece size measurement method suitable for length measurement of multilayered circuit elements with increased complexities is disclosed. This method employs a technique for changing measurement conditions in a way pursuant to either an image of workpiece or the situation of a target semiconductor circuit element to be measured when measuring pattern sizes on the workpiece image using design data of the semiconductor circuit element. With such an arrangement, adequate measurement conditions are selectable in accordance with the state of workpiece image and/or the state of a circuit element formed on the workpiece, thereby making it possible to improve the measurement efficiency. A workpiece size measurement apparatus using the technique is also disclosed.

18 Claims, 24 Drawing Sheets

| DESIGN PATTERN COORDINATES | | SEM EDGE COORDINATES | | EPE MEASUREMENT VALUE | CATEGORY |
|---|---|---|---|---|---|
| X | Y | X | Y | | |
| 540929.0 | 89833.0 | 540923.8 | 89833.0 | -5.2 | Line-Edge |
| 540929.0 | 89803.0 | 549294.7 | 89803.0 | -4.3 | Line-Edge |
| 540929.0 | 89773.0 | 540922.3 | 89773.0 | -6.7★ | Line-Edge |
| : | : | : | : | : | : |
| 540234.0 | 900234.0 | 540234.0 | 900233.0 | -1.0 | Line-End |
| 540264.0 | 900234.0 | 540264.0 | 900236.4 | 2.4 | Line-End |
| 540294.0 | 900234.0 | 540294.0 | 900239.6 | 5.6★ | Line-End |
| : | : | : | : | : | : |
| 540929.0 | 89502.0 | 540939.1 | 89510.3 | -15.0 | Outer-Corner |
| 540959.0 | 89472.0 | 540974.3 | 89473.5 | -17.1★ | Outer-Corner |
| : | : | : | : | : | : |

X: EPE1X+Overlay1-2X+EPE2X+Overlay2-3X+EPE3X≦ThX
Y: EPE1Y+Overlay1-2Y+EPE2Y+Overlay2-3Y+EPE3Y≦ThY

METHOD, DEVICE AND COMPUTER PROGRAM OF LENGTH MEASUREMENT

BACKGROUND OF THE INVENTION

The present invention relates to a pattern length measurement method and apparatus and a computer program for performing pattern length measurement. More particularly but not exclusively, this invention relates to a method and apparatus for measuring dimensions of a pattern by comparison between design data of the pattern and a real image thereof.

It is known that a pattern on semiconductor integrated circuitry is measured using computer-aided design (CAD) data. Design data such as CAD data is the one that indicates the inherently expected "ideal" shape of a semiconductor circuit element; thus, comparing the CAD data to an actually formed pattern makes it possible to evaluate a semiconductor device fabrication process. JP-A-2001-338304 (corresponding to U.S. Pat. No. 6,868,175) discloses therein a technique for performing edge detection of a pattern to be inspected and a reference pattern and for comparing detected edges together to thereby detect a deformation amount of the pattern relative to the design data.

Nowadays, semiconductor integrated circuits further advance both in miniaturization and in multilayer structure complexity, resulting in likewise improvement in performance of semiconductor device inspection apparatus. One of such semiconductor inspection apparatus is a critical dimension scanning electron microscope (CD-SEM). CD-SEM is an apparatus of the type which measures the size of a pattern formed on a workpiece based on secondary electrons obtained by scanning an electron beam on the workpiece of interest. In JP-A-2001-338304 (U.S. Pat. No. 6,868,175), it is disclosed that a pattern image formed by CD-SEM or the like is compared with its CAD data to thereby detect a deformation amount of the pattern. Unfortunately, this approach suffers from problems which follow.

On a semiconductor wafer, a large number of patterns are formed to constitute on-chip semiconductor circuit elements, such as transistors for example. For each semiconductor circuit element, its size and the dimension of a contact/junction area between patterns are determined in such a way as to realize specified performance at the stage of semiconductor device designs.

Unfortunately, the prior technique approach as taught by JP-A-2001-338304 (U.S. Pat. No. 6,868,175) is not satisfactory for performing measurement of the currently existing complicated multilayered circuit elements. One reason of this is that the prior technique approach disclosed in this Japanese patent bulletin is silent about the efficiency-increased measurement in terms of the measurement of a semiconductor circuit element with a great number of length measurement points being settable thereon due to the complexity thereof. Another reason is that the prior technique approach fails to take into consideration the fact that a semiconductor circuit element is formed to span more than two stacked layers.

SUMMARY OF THE INVENTION

One major object of the present invention is to provide a workpiece size measuring method and apparatus suitably adapted for length measurement of multilayered circuit elements with increased complexities.

According to this invention, in order to attain the foregoing object, methodology and apparatus are proposed for changing measurement conditions in a way pursuant to a workpiece image or the situation of a semiconductor circuit element to be measured when measuring pattern sizes on a workpiece image by use of design data of the semiconductor circuit element. With such an arrangement, appropriate measurement conditions are selectable in accordance with the state of workpiece image and/or the state of a circuit element formed on the workpiece, thereby making it possible to improve the measurement efficiency.

Furthermore, in accordance with this invention, it is proposed to use design data to perform length measurement between a plurality of patterns to be formed in more than two layers. With such arrangement, it becomes possible to provide the measurement method and apparatus for objectively evaluating the performance of a semiconductor circuit element and the fabrication state of an upper-level layer relative to a lower-level layer.

Other arrangements and further practical examples of the invention will become apparent from the following more particular description of modes carrying out the invention.

One major advantage of this invention lies in its ability to provide the workpiece size measurement method and apparatus suitably used for length measurement of complicated multilayered semiconductor circuit elements.

Other objects, features and advantages of the invention will become apparent from the following description of the embodiments of the invention taken in conjunction with the accompanying drawings.

DETAILED DESCRIPTION OF THE INVENTION

Figure 1:
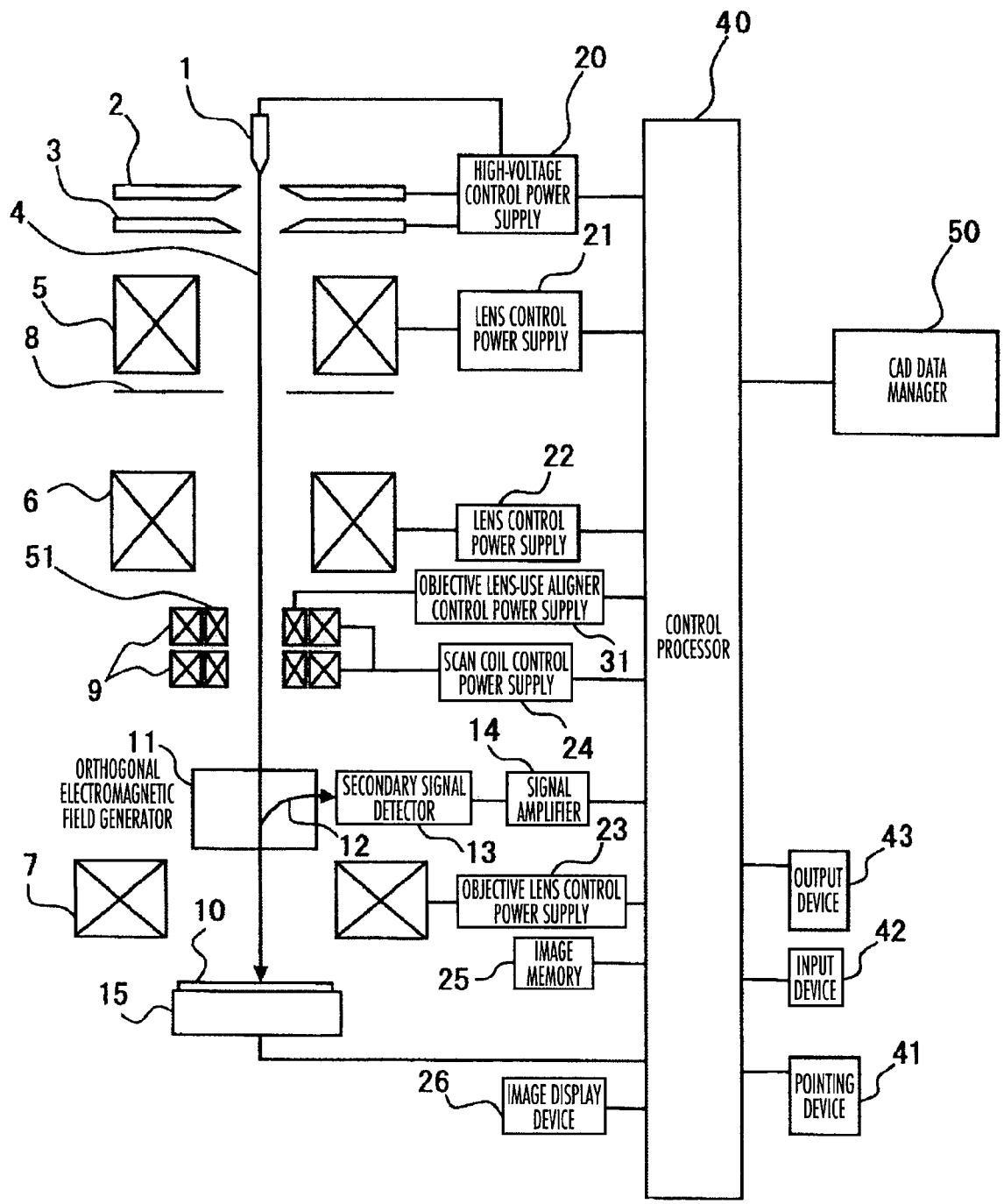
FIG. 1 is a diagram schematically showing a configuration of a scanning electron microscope (SEM).

An overall configuration of a scanning electron microscope (SEM) will be described with reference to FIG. 1 below. Between a cathode 1 and first anode 2, a voltage is applied by a high-voltage control power supply 20 under the control of a control processor 40. An acceleration voltage is applied between the cathode 1 and a second anode 3 by the high-voltage control power supply 20 under control of the control processor 40, resulting in a primary electron beam 4 being emitted from the cathode 1 and then accelerated to progress toward a lens system of the post-stage.

The primary electron beam 4 is focused by a focus lens 5 that is controlled by a lens control power supply 21. After having removed therefrom unnecessary regions of the primary electron beam by an aperture diaphragm plate 8, it is focused as a micro-spot on a workpiece 10 by the focus lens 6 that is controlled by a lens control power supply 22 and an objective lens 7 as controlled by an objective lens control power supply 23. The objective lens 7 is designable to employ various kinds of forms, such as an in-lens scheme, out-lens scheme and snorkel scheme (semi-inlens scheme). A retarding scheme is also employable, which applies a negative voltage to the workpiece to thereby decelerate the primary electron ray. Also note that each lens may be arranged by an electrostatic lens which is made up of a plurality of electrodes.

The primary electron beam 4 is two-dimensionally scanned on the workpiece 10 by a scanning coil 9 which is controlled by a scan coil control power supply 24. A secondary signal 12, such as a ray of secondary electrons produced from the workpiece 10 due to the irradiation of the primary electron beam, is guided to travel toward upper part of the objective lens 7 and thereafter is separated from primary electrons by an orthogonal electromagnetic field generation device 11 for the secondary signal separation use and then detected by a secondary signal detector 13. The signal detected by the secondary signal detector 13 is amplified by a signal amplifier 14 and thereafter transferred to an image memory 25 for visual display on an image display device 26 as a workpiece image. A two-stage deflection coil (objective lens-use aligner) 51 that is controlled by an objective lens-use aligner control power supply 31 is disposed at the same position as the scan coil 9, thereby enabling two-dimensional (2D) control of the position (field of view for observation) of the primary electron beam 4 on the workpiece 10. A stage 15 enables the workpiece 10 to move in two directions (X and Y directions) within a plane perpendicular to at least the primary electron beam.

A pointing device 41 designates a position of the workpiece image and is capable of obtaining the information thereof. There are designatable from an input device 42 image-importing conditions (scan rate, image integration number) and a field-of-view correction scheme along with the outputting and saving of an image(s). A reference numeral 43 may be a printer or any output device.

Additionally, an address signal corresponding to a memory position of image memory is generated within the control processor 40 or, alternatively, within a separately installed computer and is applied analog conversion and then supplied to the scan coil. An address signal in the X direction is a digital signal which repeats from 0 to 512 in case the image memory has a matrix array of 512 by 512 pixels as an example, whereas an address signal in Y direction is a digital signal with repeat of from 0 to 512, which is added by "+1" when the X-direction address signal reaches 512 from 0. This is converted into an analog signal.

As an address of the image memory corresponds to an address of a deflection signal for scanning the electron beam, a secondary image of a deflection region of the electron beam due to the scan coil is stored in the image memory. Note that the signal within the image memory is sequentially readable in a time-series way by a read address generator circuit that is synchronized with a read clock signal. A signal that is read out in a way corresponding to the address is analog-converted to become a luminance modulation signal of the image display device 26.

The apparatus to be explained in this example has a function of forming a line profile based on the detected secondary electrons or reflected electrons. The line profile is the one that is formed based on either an electron detection amount or luminance information of a workpiece image when performing one-dimensional (1D) or two-dimensional (2D) scanning of the primary electron beam. The line profile obtained is used for size measurement of a pattern(s) formed on a semiconductor wafer, for example.

In addition, although the explanation above of FIG. 1 is under an assumption that the control processor 40 is integral with the SEM or arranged in a way similar thereto, this is not restrictive of the invention with no doubt and may alternatively be arranged so that a processor provided separately to the SEM structure is used to perform processing as will be described later. In such case, it becomes necessary to provide a transfer medium for transmitting to the processor a detection signal to be detected by the secondary signal detector as an image and for transmitting a signal(s) from the processor to a lens or a deflector of the SEM along with input/output terminals for inputting and outputting a signal(s) being transmitted via the transmission medium.

The apparatus of this example further comprises a function of prestoring as a recipe certain conditions when observing a plurality of points on the semiconductor wafer as an example (such as measurement portions, optical conditions of SEM, etc.) and a function of performing measurement and observation in deference to the contents of such recipe.

An arrangement alternative to the approach above is that a software program for performing processing to be later described is registered in a recording medium and is executed by a processor operative to supply a necessary signal(s) to the SEM or else. In other words, examples to be later explained may also be implemented by use of a program or a program product that is employable in charged-particle beam apparatus capable of acquiring an image(s), such as SEM or like equipment.

Also note that a CAD data management unit 50 may be connected to the control processor 40, which unit is for storing design data of patterns on a semiconductor wafer and for performing conversion to data necessary for the control of SEM. The CAD data manager 50 has a function of preparing, based on CAD data as input thereto, recipe for control of SEM. It also has a function of rewriting the recipe based on a signal to be transmitted from the control processor 40. Alternatively, the processing to be later explained may be performed by a processor which is provided within the CAD data manager 50. Further, the processor provided in the CAD data manager 50 is used in place of the control processor 40 to control the SEM.

Note here that although the explanation is given under the assumption that the CAD data manager 50 is a unit separate to the control processor 40, this is not to be construed as limiting the invention. The CAD data manager 50 may alternatively be a unit integral therewith.

In this example the workpiece 10 is a wafer in the process of manufacturing semiconductor device products. A resist pattern is used, which was lithographically formed on the wafer. Used as its comparative object was semiconductor circuit design data (CAD data) that becomes the original of such pattern.

The semiconductor circuit design data used here is an ideal pattern shape, which is finally desired as a semiconductor circuit pattern. Note that although the explanation below assumes that the object to be inspected is a semiconductor wafer, this is not an exclusively limitative one and is replaceable by others as far as the design data and the object to be evaluated make a pair. Additionally, any type of circuit design data is usable in so far as a software application for displaying the circuit design data has displayability in the format thereof while dealing with it as graphics data.

Embodiment 1

An example for measurement of the distance between an edge portion of scanning electron microscope (called SEM edge hereinafter) and design data will be explained with reference to some of the accompanying drawings below. This example will be referred to as Edge Placement Error (EPE) measurement in some cases.

Figure 2:
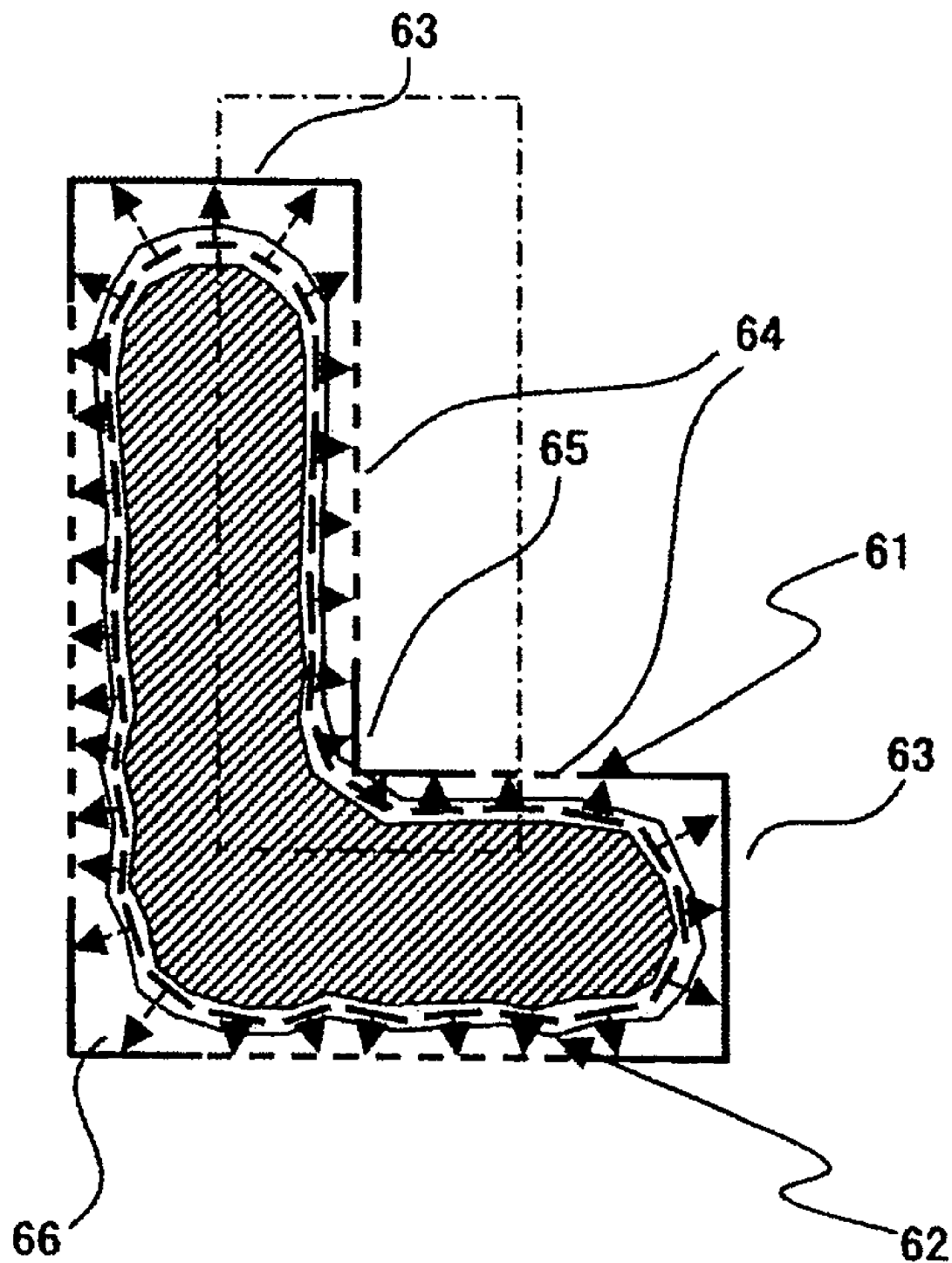
FIG. 2 is a diagram showing a state that design data and a SEM image are laid over each other.

FIG. 2 is a diagram showing a state in which the design data and a SEM image are laid over each other. While EPE measurement is the one that measures the distance between design data and SEM edge, it is often the case that the real semiconductor circuit element is formed so that a rectangular corner of pattern is deformed and corrupted into a rounded shape, for example. Upon execution of EPE measurement for such corner-rounded pattern, it is sometimes difficult to judge the exact direction along which the measurement is to be done.

In this example, in view of such problem, it is proposed to determine the length measurement direction when performing EPE measurement in accordance with the SEM edge forming direction. This embodiment will be explained in detail using an example which performs EPE measurement between design data 61 and SEM edge 62 with reference to FIG. 2 below. FIG. 2 is a diagram for explanation of the example which performs the measurement of SEM edge 62 in all directions. In the example shown in FIG. 2, measured portions are categorized into (1) tip ends of a line pattern (referred to as line ends 63 hereinafter), (2) line side portions (referred to as line edges 64 hereinafter), (3) inside of a bent portion of the pattern (referred to hereafter as inner corner 65), and (4) outside of the pattern bent portion (referred to as outer corner 66 hereafter).

The reason for this categorization is that each pattern portion is different from the others in importance and pattern deformation factor, which makes it necessary to perform evaluation in deference to such importance and deformation factor. For example, regarding the line ends 63 and line edges 64, it is needed to evaluate the line ends 63 more strictly (with lessened allowable errors) in case the line end 63 is brought into contact with another pattern, not shown. Additionally, an Optical Proximity Correction (OPC) pattern is added in some cases to the pattern corner in order to suppress unwanted pattern deformation, and this necessitates different evaluation between the portion and line edge.

As stated above, the categorization in units of pattern segments is very important for execution of the evaluation of EPE measurement values. In this example, in order to accurately determine the pattern measuring direction per pattern segment, it is proposed to set the length measuring direction at a specific direction that is perpendicular to SEM edge.

Figure 3:
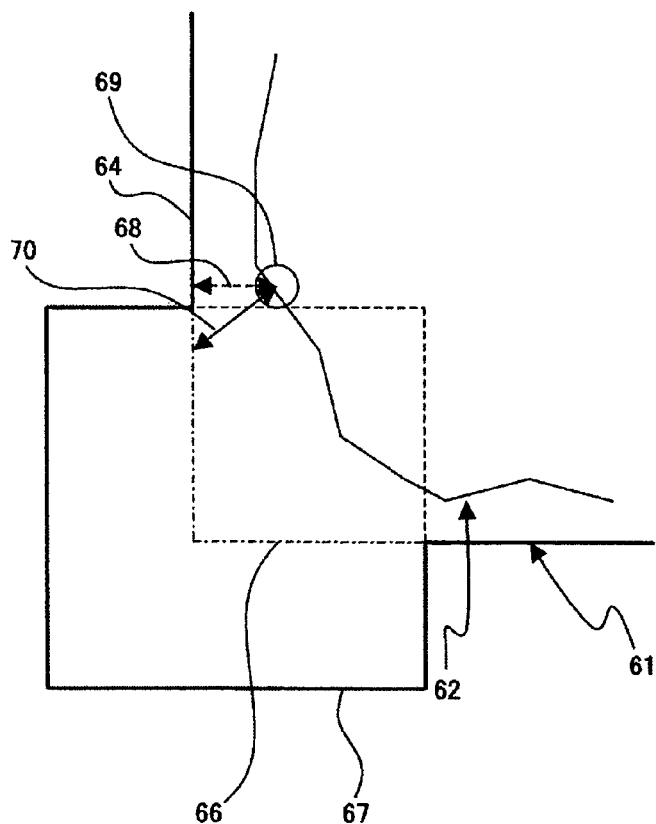
FIG. 3 is an enlarged diagram of nearby part of an outer corner of FIG. 2.

FIG. 3 is an enlarged view of a portion of the pattern shown in FIG. 2, including the outer corner 66 and its nearby part. Assuming that the length measurement direction is determined to the perpendicular direction with design data being as a reference, this length measurement direction will be determined to be a direction such as a length measurement direction 68. This would result in a length measurement reference point 69 being categorized unintentionally as a length measurement point belonging to the line edge 64.

However, the length measurement reference point 69 should inherently be categorized so that it belongs to the outer corner 66. This can be said because the length measurement reference point 69 is apparently a portion which was formed due to the fact that the pattern corner is unintentionally rounded on account of certain causes, wherein it is significantly different in deformation factor from the line edge 64.

It has been stated that respective pattern segments are individually different from one another in deformation factor and importance thereof; and, from the viewpoint of size evaluation, it is desirable to manage length measurement results with categorization applied thereto.

To this end, this example is specifically arranged to set the length measurement direction 70 at a perpendicular direction to SEM edge 62. With this setting, it becomes possible to set the length measurement direction at a correct direction as derived from the deformation factor of the pattern while at the same time enabling achievement of appropriate categorization of EPE length measurement results.

Figure 4:
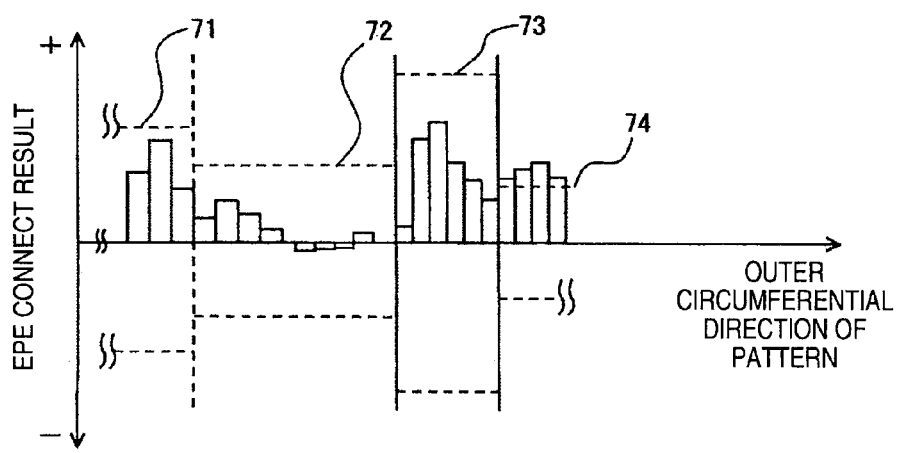
FIG. 4 is a diagram graphically showing results of length measurement of a pattern in all directions.

An explanation will be given of a further example in the case of the EPE length measurement being performed in all directions. FIG. 4 is a diagram graphically showing all-direction length measurement results of the pattern of FIG. 2. The graph of FIG. 4 demonstrates some extracted length measurement results of a pattern portion indicated by dash-and-dot lines in FIG. 2 (Note that the length measurement results of FIG. 4 per se do not always coincide with the length measurement results of FIG. 2).

In the example shown in FIG. 4, the threshold value of allowable errors is made variable in units of categories of pattern segments. With the setup of the allowable error value of EPE measurement per pattern segment category, it is possible to prevent increase in measurement point number otherwise occurring due to mere routine evaluation of EPE measurement results or oversight of a measurement point to be inherently evaluated. Threshold values 71, 72, 73 and 74 are given to the line end 63, line edge 64, inner corner 65 and line edge 67, respectively.

In the case of this example, the allowable error value of line edge 64 is set less than that of inner corner 65. This is in light of the fact that the corner is deep in the edge vertical direction with respect to the edge portion so that the risk of line cut-off or else stays less regardless of slight size variations.

Figure 21:
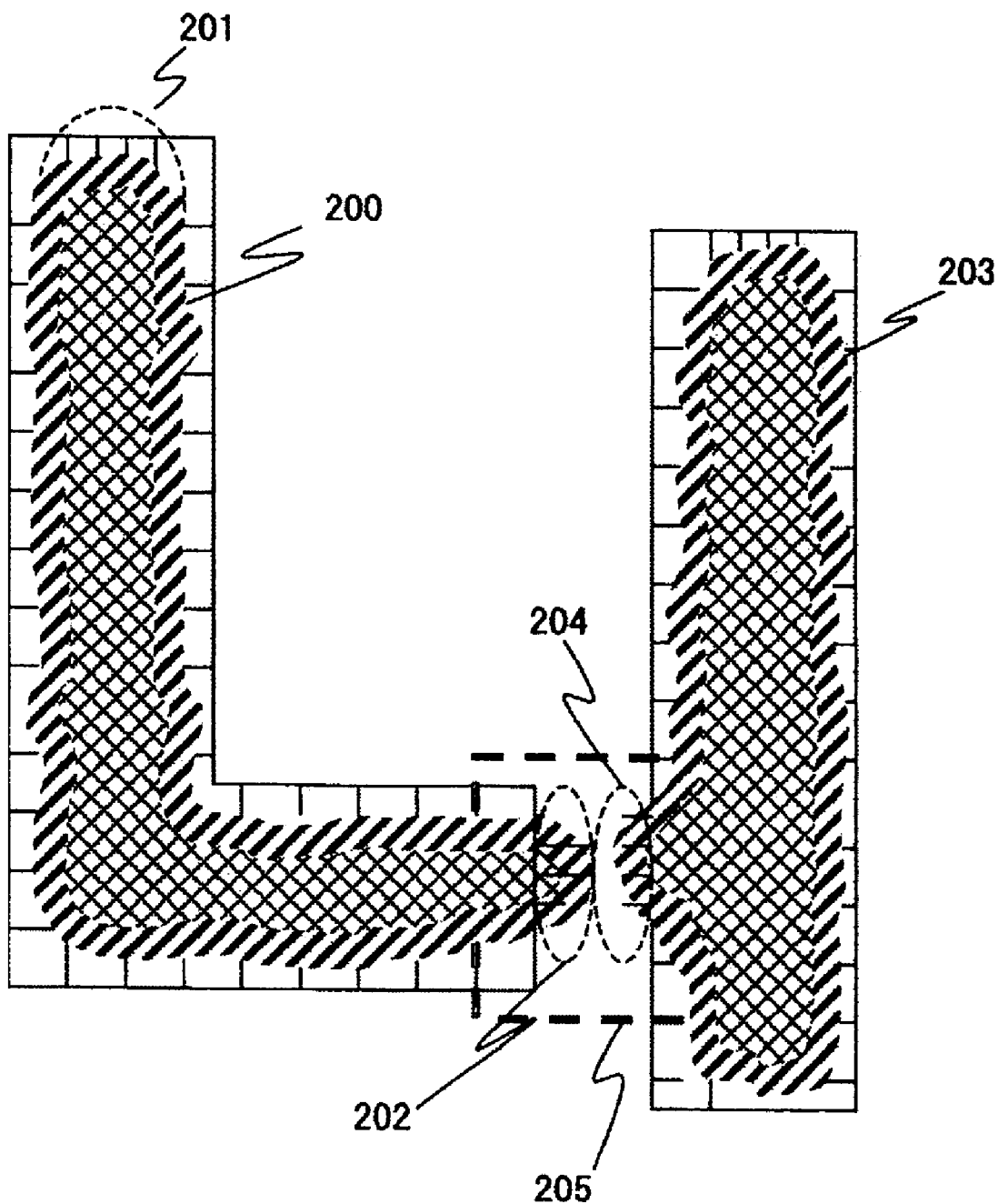
FIG. 21 is a diagram for explanation of a scheme for categorizing EPE measurement results in the case where two patterns are placed adjacent to each other.

Additionally, as depicted in FIG. 21, in case two patterns 200 and 203 are placed adjacent to each other, a line end 201 and line end 202 are different from each other in importance of size accuracy. The line end 202 is positioned in vicinity of a line pattern 203 so that these can come into contact together in a way depending upon the value of a pattern formation error. The same goes with a portion 204 of the line pattern 203, which is different in importance of size accuracy from other line edges. In particular, regarding a portion with the risk of contact among the patterns involved, managing more strictly than the other portions (e.g., setting the allowable error amount to stay less) makes it possible to promptly take corrective action to improve the yield and throughputs in semiconductor device manufacturing processes.

An alternative approach is to use a program for registering as a hot spot an adjacent portion 205 of two patterns to thereby perform more strict size management when EPE measurement portion overlaps this hot spot or perform adjustment of measurement items in an automated way, such as increasing the number of measurement point. This makes it possible for an operator to perform setup of measurement items (preparation of a recipe) in a more simplified manner. In FIG. 21, dot-line indication is used to make visually distinguishable the measurement points that are set within the portion 205. If the measurement portions are distinctly displayed on a display device in conformity with the importance of length measurement portions in this way, it becomes possible for the operator to affirm on the display screen the adequacy of the measurement positions and the number of length measurement points.

Figures 7, 8:
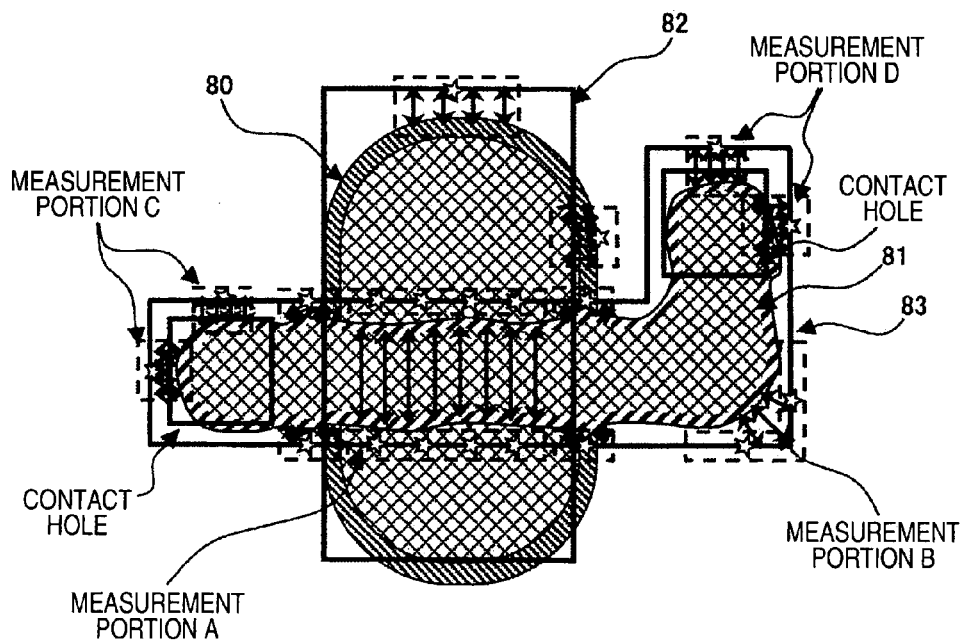
FIG. 7 is a diagram for explanation of an example which displays, in a table form, all-direction EPE measurement results.
FIG. 8 is a diagram for explanation of an example which performs EPE measurement with respect to a multilayer of several patterns which make up a semiconductor circuit element.

As apparent from the foregoing discussion, setting different allowable error values in units of pattern-different regions makes it possible to perform adequate size management pursuant to the importance per pattern segment. Note here that in the case of this example, an arrangement is employable which stores the all-direction EPE measurement results in a table form as shown in FIG. 7 and which distinctly displays certain EPE measurement result with its value exceeding the preset allowable error value while letting it be distinguishable from the other measurement results to thereby clarify the pattern to be reevaluated. In the case of the example of FIG. 7, "black star" mark is displayed at EPE measurement results to achieve visual distinguishability from the other measurement results. With such an arrangement, an administrator is able to selectively evaluate only certain portions with their errors exceeding the allowable error level, which leads to improvement in evaluation efficiency.

Furthermore, as has been described in conjunction with FIG. 2, it becomes possible by execution of the all-direction EPE measurement to perform judgment as to whether the pattern per se is offset relative to the design data or whether the pattern is partly deformed. As a result of the all-direction EPE measurement, if a significant error is found only at a portion, it is considered that only such region is deformed due to some reasons. However, for example, in a case where an EPE measurement value in a direction exhibits a large negative number whereas an EPE measurement value on the opposite side in the direction has a large positive number, there is a possibility that such pattern is formed with appreciable offset along the positive polarity direction.

By performing the EPE measurement in all directions such as shown in FIG. 2, it becomes possible to judge whether the pattern is partly deformed or whether this pattern per se is formed with displacement. In this case, it is considered to provide threshold values different from the threshold values 71 to 74. For example, a first threshold value is provided at a pattern segment in the first direction of the pattern; a second threshold value is provided at a pattern segment on the opposite side in this direction. In this case, the first threshold value and second threshold value are set so that these are opposite in polarity to each other. Under such condition, when the threshold value of an EPE measurement result is in excess of any one of the first and second threshold values, it is presumable that the pattern formed is offset in either the first direction or in the second direction.

A length measurement process of this example will be described using FIG. 5 below. Firstly, a recipe with measurement points and optical conditions of SEM being prestored therein is read into the control processor 40 in responding to receipt of an instruction from the input device (at step S0001). Then, the control processor 40 sets up image acquisition parameters and SEM optical conditions on the basis of the recipe thus read at S0001 (S0002). Based on the setup image acquisition parameters and SEM optical conditions, a SEM image is acquired (S0003).

Next, edge extraction of the SEM image is performed based on the SEM image acquired. In the processing of this portion, an edge emphasis filter such as for example sobel filter is used (S0004). Next, design data corresponding to the SEM image acquired is read out (S0005).

Upon execution of length measurement between the design data and SEM edge, in order to perform position alignment therebetween, position alignment between the both is executed with reference patterns owned by both the SEM image and the design data (e.g., alignment marks provided to obtain a highly magnified SEM image) being as a reference. In the event that ordinary pattern-matching position alignment is performed for an object pattern to be measured, it will possibly happen that it becomes impossible to execute accurate EPE measurement; in view of this, pattern matching between the reference patterns owned by both the SEM edge and the design data is executed to thereby perform the length measurement pattern position alignment of SEM edge and design data (S0006).

Next, for a length measurement reference position 61 on the design data being recorded in the recipe, image processing is performed to search a measurement reference position 63 on SEM edge having its perpendicular line crossing over the measurement reference position (S0007). In the case of this example, such measurement reference position search is conducted relative to all directions of the pattern. Then, length measurement is done between the searched measurement reference position 63 on SEM edge and the measurement reference point 61 on design data (S0008).

Although in the case of this example a specific example is explained for searching the measurement reference position 63 based on the measurement reference position 61, this is not a limitative one and may alternatively be arranged, for example, in a way which follows: after having obtained SEM image, any given SEM edge on SEM image is designated by the operator using the input device or else for performing length measurement between this SEM edge and a contour of design data that is positioned on the perpendicular line of such SEM edge.

Next, comparison with a threshold value assigned is performed in units of categories of pattern portions (S0009). In the case of this example, the threshold values 71-74 are compared with EPE measurement results. The result of this is stored in a table form while causing a threshold value-exceeding measurement result to be distinguished from the other measurement values; alternatively, only such threshold value-exceeding measurement result is stored (S0010). When displaying this length measurement result, if an arrangement is employed for performing distinguishable displaying such as color differentiating, blinking or the like with respect to the other length measurement results, it is possible for the operator to specify, through visual checking, his or her intended length measurement portion to be reevaluated.

Next, in order to compare whether the pattern is partly deformed or whether the pattern itself is formed with positional offset, judgment is made to determine whether EPE measurement results in a specific direction of the pattern and in the opposite direction are each in excess of a prespecified threshold value and, simultaneously, whether the direction of such offset is reversed in positive and negative polarities (S0011). This judgment result may also be stored in a table form and displayed to indicate that the pattern is offset when the need arises.

Figure 22A:
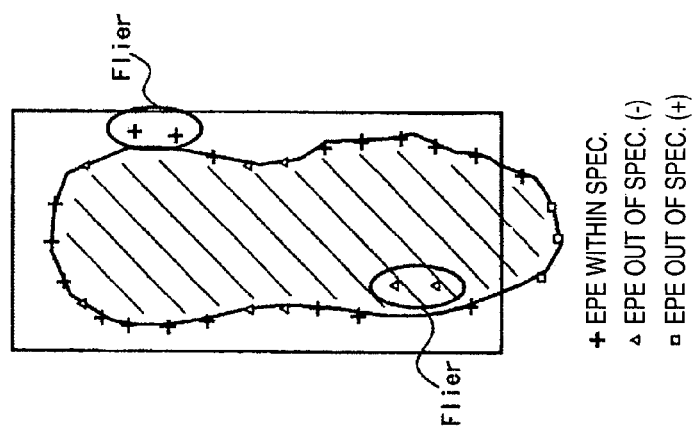
FIGS. 22A to 22D are diagrams each showing an exemplary on-screen display image of EPE measurement result.

FIGS. 22A to 22D are diagrams for explanation of display examples of EPE measurement results. FIG. 22A shows an example which displays an execution result of EPE measurement between a detected SEM edge 221 and design data 222 while laying it over SEM edge and/or design data.

A dotted line 223 indicates a length measurement location at which EPE measurement result falls within specifications (i.e., length measurement portion falling within a prespecified error range (threshold value) when compared to its ideal value). A dash-and-dot line 224 is a length measurement location at which EPE measurement result is out of the specifications and indicates a length measurement portion at which it becomes a negative length measurement result when compared to the ideal value. A solid line 225 is a length measurement location at which EPE measurement result is out of the specifications and indicates a length measurement portion at which it becomes a positive length measurement result in comparison with the ideal value.

By displaying the length measurement results while distinguishing between those within the specifications and the others out of the specifications, it is possible for the operator to selectively ascertain the individual measurement value that becomes out of the specifications, thereby making it possible to readily realize the decision of semiconductor process conditions.

In particular, in case the all-direction length measurement is performed for a pattern in the way of this example, it becomes possible to easily judge, through visual check, whether the pattern per se is deviated in formation position or whether EPE measurement result is out of the specifications due to the deformation of such pattern.

In addition, all-direction length measurement results are subjected to calculation of an average value in units of chips or SEM shots on a per-direction basis, thus causing a calculated result to be displayed in the form of a wafer map in units of chips or on a per-shot basis. With this scheme, it becomes possible to visually verify the all-direction length measurement results in unit of chips or shots while comparing them to those of other chips or shots.

Figure 23:
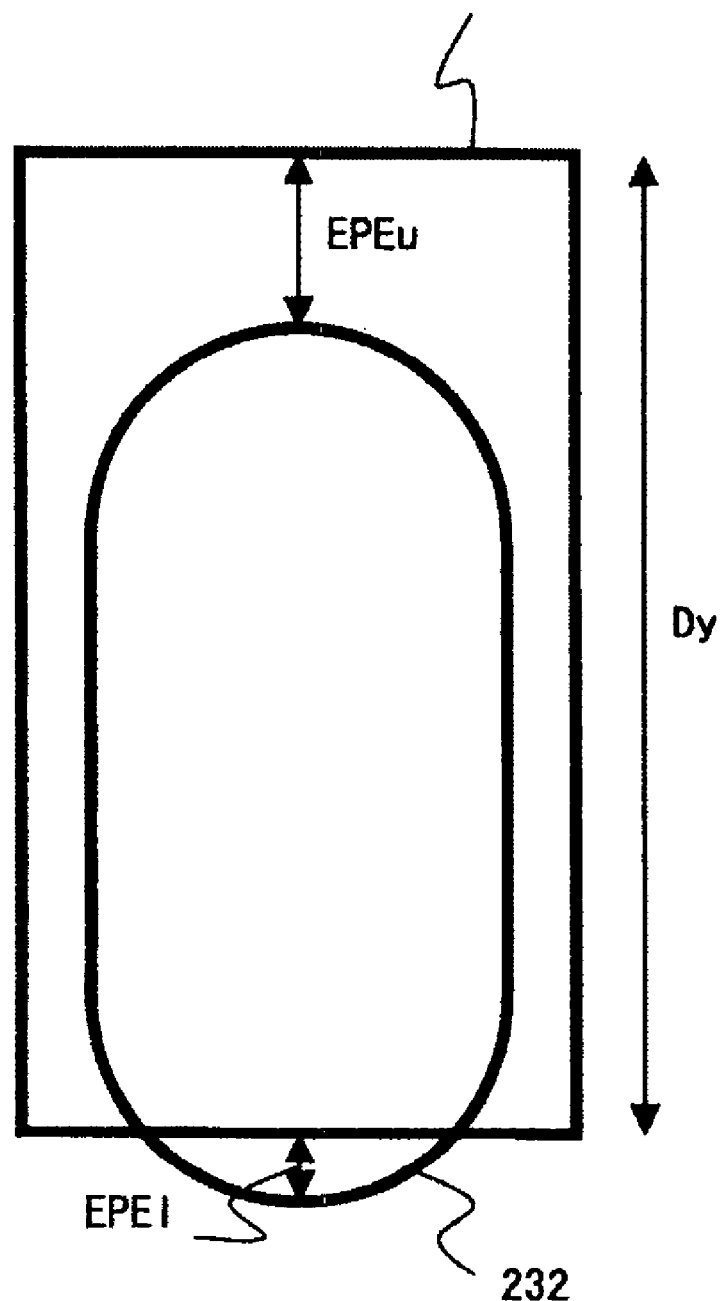
FIG. 23 is a diagram for explanation of an example in which a SEM edge is deviated in position relative to design data.

Further, as shown in FIG. 23 for example, in case a SEM edge 232 is offset relative to design data 231 in the downward direction on the drawing sheet, a need is felt to specify the factor(s) of the SEM edge 232 being deviated unintentionally relative to design data 231; however, there is a case where its importance differs depending on the degree of a change of the largeness of SEM edge with respect to the largeness of design data. For example, when the size of SEM edge is very small when compared to the design data (e.g., Th1<|Dy−(EPEu+EPEl)|), the pattern shift amount in the downside direction of FIG. 23 becomes extremely larger when compared to a state that a size difference between SEM edge and design data is kept less even when supposing that EPEl is the same in value. Thus, it is recommendable to display length measurement portions while distinguishing between the case of Th1<|Dy−(EPEu+EPEl|) and the case of Th1≧|Dy−(EPEu+EPEl)1.

The same goes with an event for displaying in a wafer map style. Using an arrangement for displaying information of the largeness of a pattern relative to design data and information concerning the shift amount of SEM edge in an overlay fashion, it becomes possible, even when the same EPE measurement result is obtained, for the operator to judge the seriousness thereof through visual check.

Figure 22B:
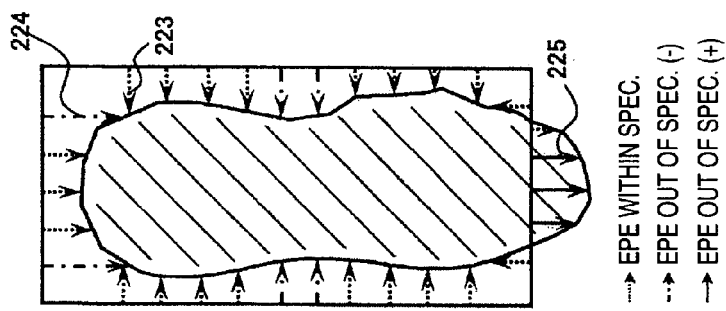

FIG. 22B is a diagram showing an example which displays SEM edge while distinguishing between those within the specifications and the others out of the specifications (plus and minus) in place of the display example using arrows in FIG. 22A. In this example, in the case of an EPE measurement result within the specifications is obtained, this SEM edge is displayed by dotted line; in case an EPE measurement result out of the specifications (minus) is obtained, such SEM edge is displayed by dash-and-dot line. In case an EPE measurement result out of the specifications (plus) is obtained, this SEM edge is displayed by solid line. By distinguishably displaying the lines indicative of SEM edges based on the EPE measurement result in this way, it becomes possible to judge through visual check the tendency of length measurement results.

Figure 22C:
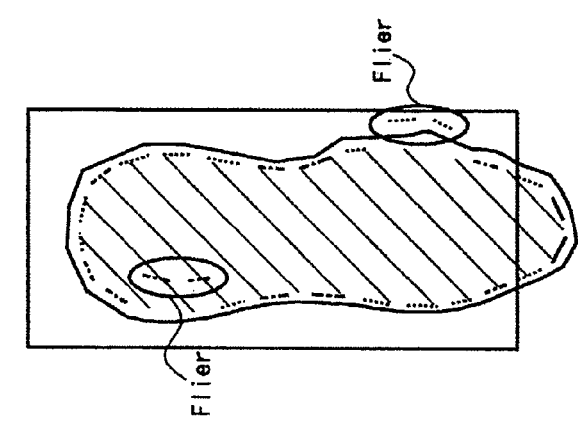

FIG. 22C is a diagram for explanation of an example which defines the direction of EPE measurement with design data being as a reference. While in FIG. 22A the length measurement direction is determined to extend toward the vertical direction relative to SEM edge for execution of the length measurement between SEM edge and design data, the example of FIG. 22C is such that the length measurement direction is set to a direction perpendicular to the design data. With such the length measurement direction changeover while performing switchable display of those within the specifications and the others out of the specifications based on EPE measurement result, the operator is enabled to judge which direction is appropriate for setup of the length measurement direction while at the same time verifying the real SEM edge.

Figure 22D:
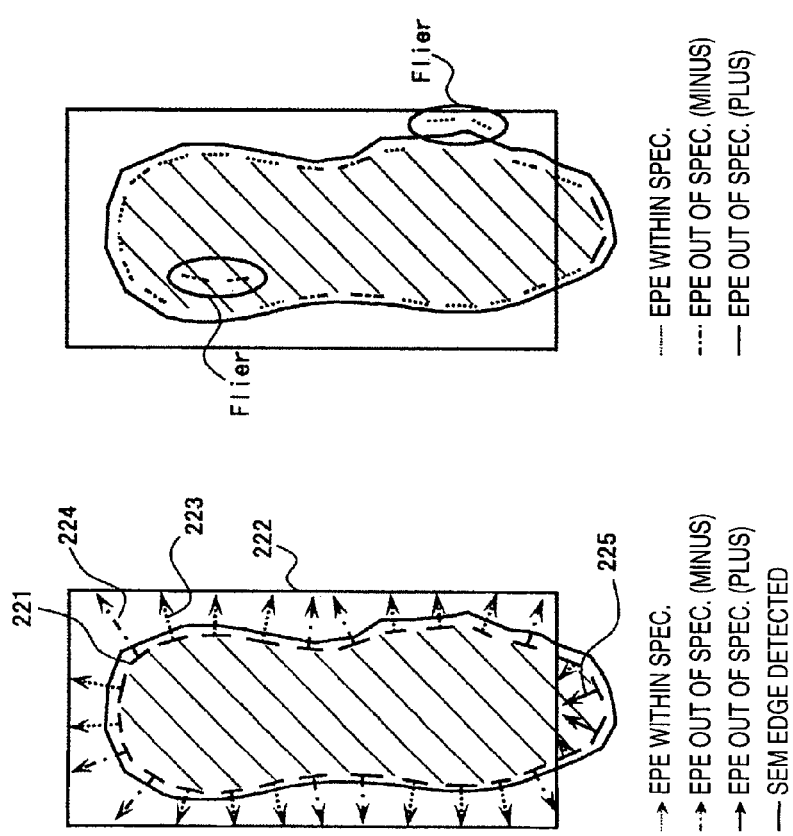

FIG. 22D is the one that uses cross, triangle and rectangle marks in place of the line display of FIG. 22B to display EPE measurement results within the specifications, length measurement results out of the specifications (minus) and length measurement results out of the specifications (plus), respectively. This example is not to be construed as limiting the invention, and any other marks having various shapes are applicable as far as these marks per se have shapes that reflect length measurement results.

Embodiment 2

An explanation will be given of an example which determines sampling points based on a length measurement result between design data and a Scanning Electron Microscope (SEM) edge, with reference to some of the accompanying drawings below. As shown in FIG. 2, when performing Edge Placement Error (EPE) measurement of a single pattern, a great number of candidates for the length measurement reference position are considered. However, the evaluation of a pattern from among all the measurement reference position candidates consumes much time and requires troublesome manual operations—this is not preferable in a viewpoint of measurement efficiency. On the other hand, it is very difficult to predetermine how a pattern will change from its ideal shape (design data): there is no guarantee that a measurement reference position as set up by a recipe is always the adequate length measurement location.

In this example, in view of the above-noted problem, it is proposed to perform length measurement between design data and SEM edge at more than two portions and to regard as a sampling point a portion with its length measurement value exceeding a prespecified threshold value. More specifically, in view of the fact that a portion with its size greatly changed from the design data is important as an evaluation object, this portion is selectively subject to sampling to thereby improve the measurement efficiency.

A length measurement process of this example will be explained using FIG. 6. Note that explanations of similar steps to those in FIG. 5 are eliminated herein. First, in a similar way to the example of FIG. 5, the control processor 40 acquires a SEM image based on optical conditions being stored in the recipe (at steps S0001 to S0003).

EPE measurement is performed between the SEM image thus acquired and the design data (S0007). A plurality of measurement reference positions (35 points in the case of the example of FIG. 2) are set on the design data, so length measurement is done between them and SEM edges in units of the measurement reference positions. Multiple length measurement results obtained in this way are each compared to a predefined specific value (threshold value) (S0007). As a result of this comparison, let a portion exceeding the specific value be a sampling point, causing its length measurement result to be stored in a storage medium along with position information of length measurement portion (S0008).

Selectively performing the sampling of those portions exceeding the predefined value makes it possible to efficiently execute subsequent pattern evaluation. It is noted that although in this example one example is explained which selectively stores only the information as to certain length measurement portions exceeding the predefined value, this is not restrictive of the invention. For instance, in the case of FIG. 2, in an arrangement which stores length measurements in all of 35 points, a flag may be set to the length measurement position information to facilitate the understanding that which point is the point exceeding the predefined value to thereby enable easy judgment of such length measurement points during evaluation later. Flags indicative of a length measurement point and length measurement position and also whether it exceeds the predefined value or not may be stored in a table form—for example, as depicted in FIG. 2, these may be distinguishably displayed on the superposed image of SEM image and design data while comparing predefined value-exceeding length measurement positions to the other length measurement positions (in the case of FIG. 2, this is arranged so that a broken line is used to distinguishably display the predefined value-exceeding length measurement points).

Embodiment 3

An example which categorizes length measurement results based on the state of design data concerning length measurement positions thereof will be explained with reference to some of the drawings below. FIG. 8 shows an example with a plurality of patterns being formed into a multilayered structure and is a drawing showing a display example wherein design data 82, 83 of an under layer and target layer are laid over a SEM image of a pattern having a poly-gate (target layer) 81 that is multilayered above an active area (under layer) 80.

When performing EPE measurement for a composite pattern making up a semiconductor circuit element, a very large number of measurement reference position candidates exist. However, it is not preferable in the viewpoint of measurement efficiency to evaluate the pattern based on length measurement results of all such measurement reference position candidates consumes much time and labors.

Below is an explanation about an example which relies upon the knowledge that a portion determining the performance of a semiconductor circuit element is important as an object to be measured whereas a portion that does not appreciably affect the performance of the semiconductor circuit element is low in importance as the object under measurement and which categorizes, when performing length measurement of a pattern constituting a semiconductor circuit element, length measurement results in accordance with states of design data at length measurement positions to thereby discriminate between length measurement results being important as evaluation objects and the remaining ones and thus realizes semiconductor device evaluation using SEM image at enhanced efficiency.

More specifically, in this example, an explanation will be given of a technique for performing categorization of length measurement results in units of segments of design data.

In the case of FIG. 8, a length measurement portion A is a part at which the active area and poly-gate overlap each other and is very important as an object to be measured. On the other hand, a length measurement portion B is a part that does not greatly affect the transistor performance even if it becomes slightly thinner. In this way, even one poly-gate changes in its importance in accordance with the state of design data thereof (in particular, the relationship with another pattern connected thereto).

Figure 9:
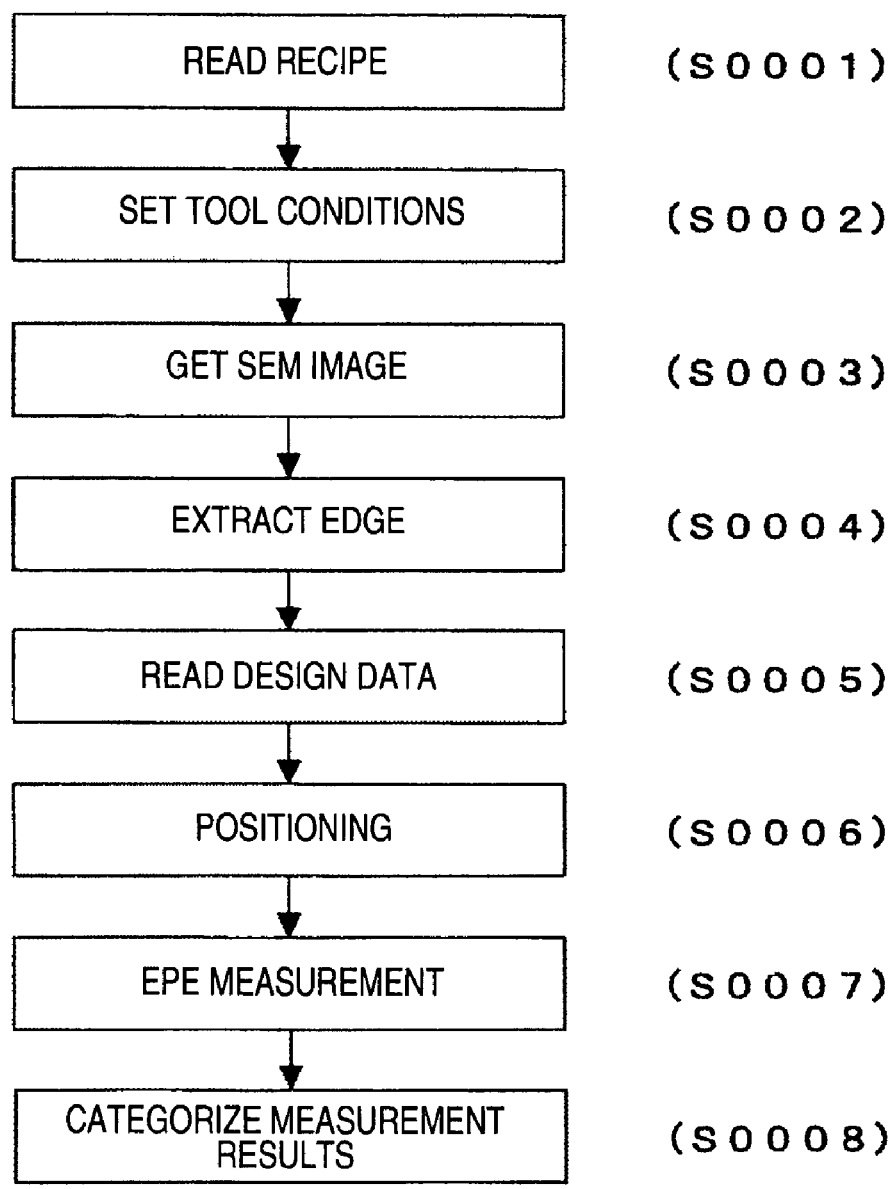
FIG. 9 is a flowchart of a procedure for categorizing EPE measurement results.

This example proposes, as a tool for evaluation of the performance of semiconductor circuit element, to select and register a length measurement result per characteristic position of design data. Referring to FIG. 9 a process of selecting or "screening" a length measurement result(s) of this example will be set forth below.

Figure 5:
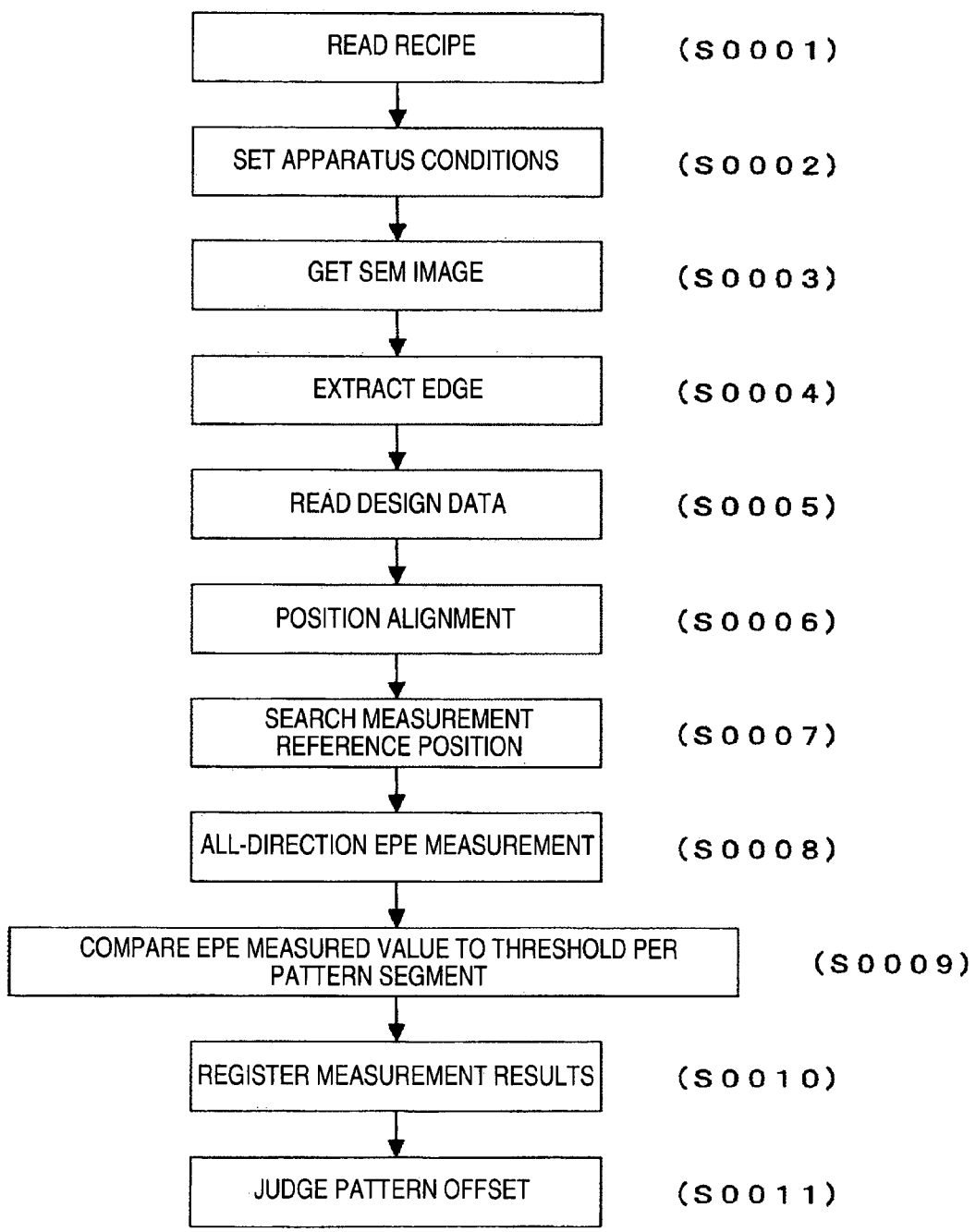
FIG. 5 is a flow chart for explanation of one example of EPE measurement.
Figure 6:
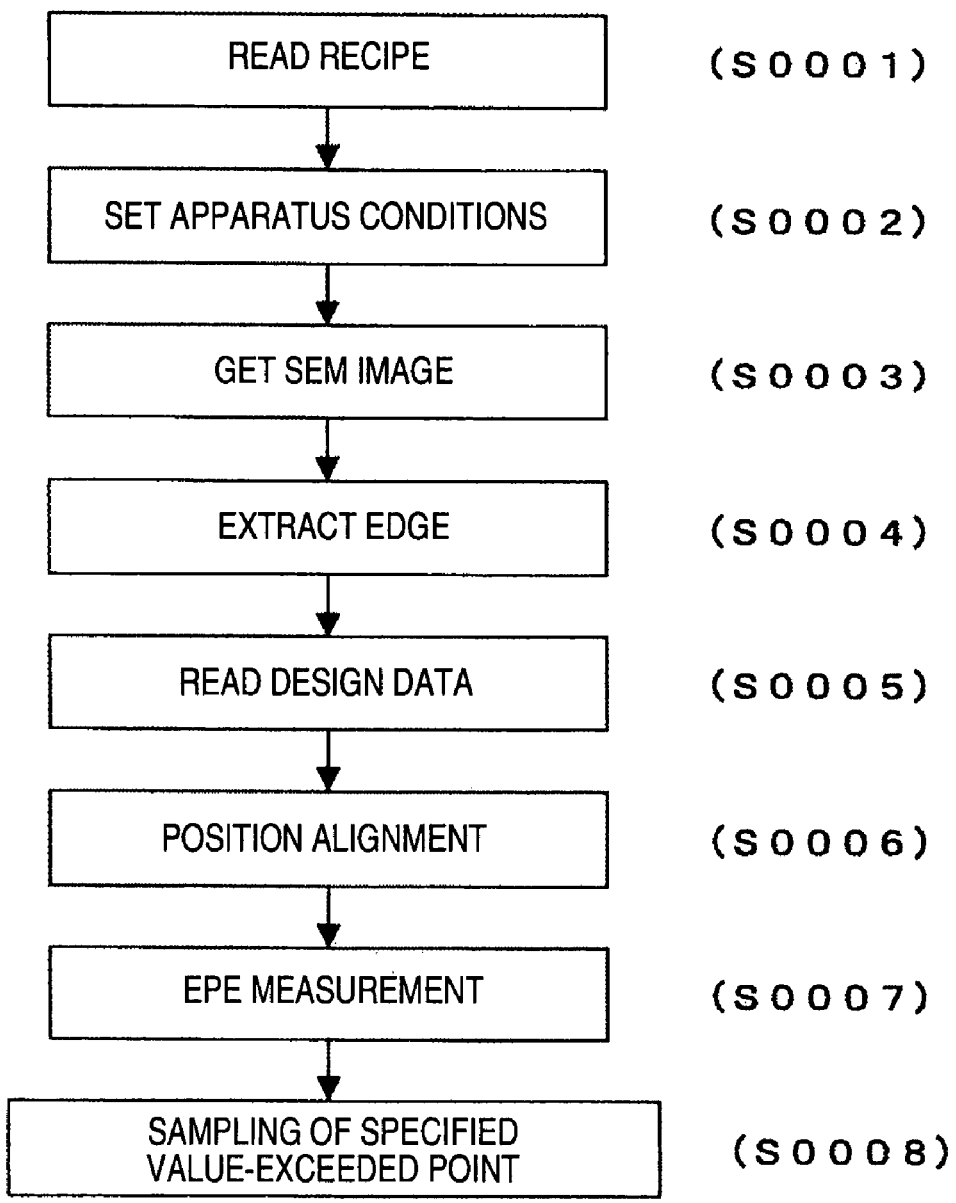
FIG. 6 is a flowchart for explanation of an example which selectively performs sampling of an EPE measurement result that exceeds a predetermined value.

Firstly, in a similar way to FIG. 5 or else, the control processor 40 acquires a SEM image based on optical conditions being stored in the recipe (S0001 to S0003). EPE measurement is performed between the SEM image acquired and the design data (S0007). A large number of measurement reference positions are set on the design data, and length measurement is performed between each of the measurement reference positions and SEM edge. Note here that although in the case of this example the explanation assumes that the measurement positions are registered in the recipe, this is not an exclusive one and any given setting may be done by the input device on the overlay display screen of SEM image and design data.

A plurality of length measurement results obtained at the step S0007 are categorized in a predetermined way or, alternatively, based on information of a circuit element(s) to be obtained from the design data (S0008). For example, in the case of gate pattern 81 of FIG. 8, the measurement results are divided roughly into three categories: first, a length measurement portion A concerning part that overlaps an active area; second, a length measurement portion B relevant to part that does not overlap the active area; and third, a length measurement portion C concerning part that overlap a contact hole to be formed in an upper layer of a target layer.

As previously stated, the length measurement portion A is a very important object to be evaluated. In contrast, the length measurement portion B is low in order of priority as the evaluation object as stated above. Further, a length measurement portion C varies in importance depending on the kind of a pattern to be formed in the upper layer. Note that an explanation below assumes that the length measurement portion C is an important length measurement portion in view of the relationship with the pattern to be formed in the upper layer whereas a length measurement portion D is a pattern which is low in order of priority for evaluation in light of the relationship with the pattern being formed in the upper layer. In this way, according to this example, it is possible to evaluate the circuit element after completion of categorization into important evaluation objects and the others. This has an effect in improvement of the measurement efficiency.

Although in the example explained above the length measurement portions are categorized in units of circuit element states, it may alternatively be arranged to merely add a mark indicating that each length measurement result belongs to which one of the categories. Another way is to store the length measurement results for measurement positions in a table form and add to this table an identification mark or the like which indicates a length measurement result belongs to which category. Additionally, while various ones are employable as the genre of such categorization, one example is to classify broadly by "part appreciably affecting the characteristics of a semiconductor circuit element" and "the remaining parts." Another approach is to classify broadly by "contact portions with another pattern (or, portions expected to come into contact therewith)" and "the other portions". Combinations thereof are not limited to two, and may be three or more. Further, a variety of new kinds of genres may be combined together to create new categories.

Figure 10:
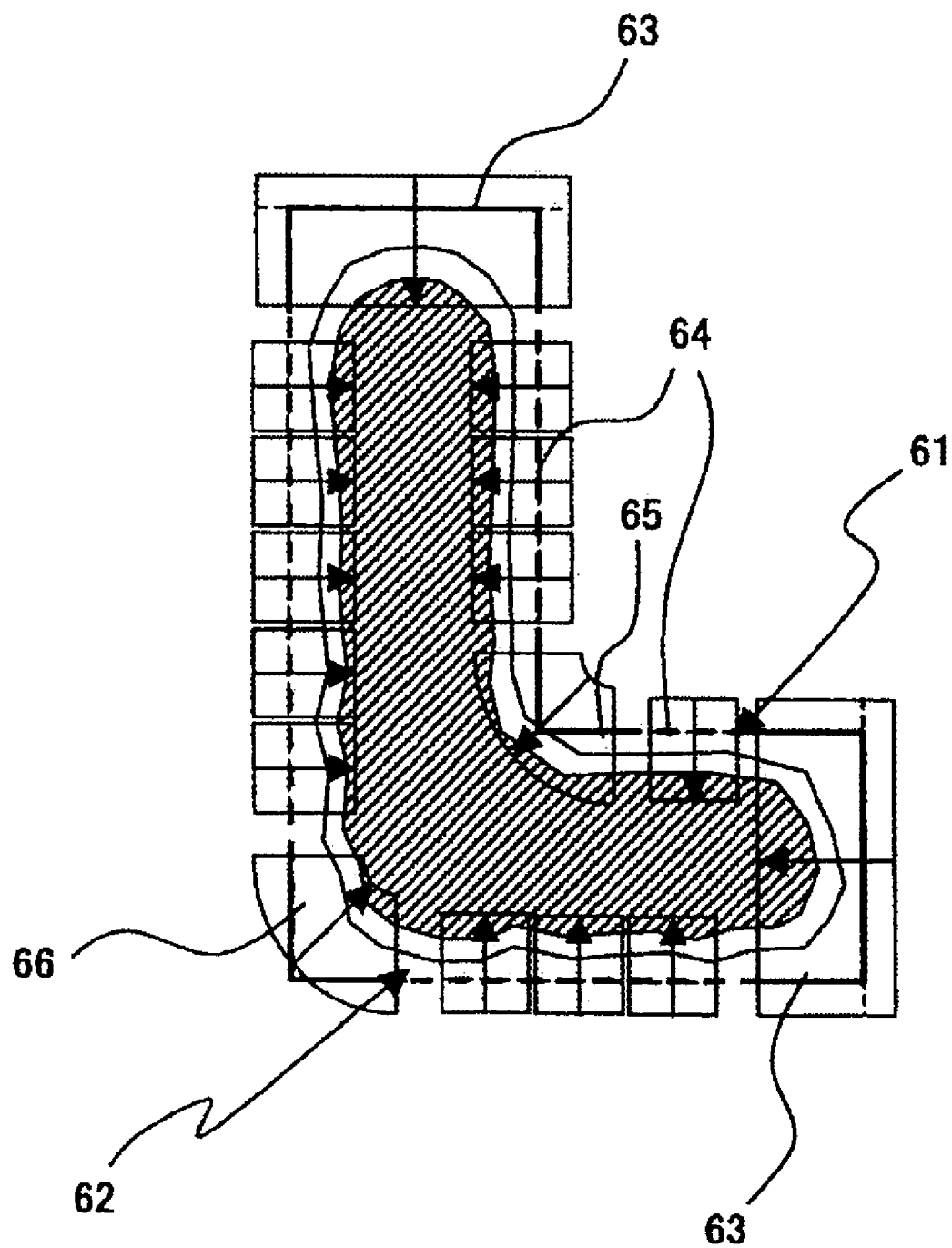
FIG. 10 is a diagram for explanation of an example which determines an EPE measurement direction with design data being as a reference.

FIG. 10 is a diagram showing an example which determines a length measurement direction with design data 61 being as a reference, in regard to the EPE measurement of the pattern used in the explanation of FIG. 2. In the case of this example, the length measurement direction is set to a direction which is perpendicular to the design data 61. Note however that the length measurement direction is set so that an outer corner 66 and an inner corner 65 are each directed from a crossing point of two straight lines forming a corner toward a direction of 45° relative to the individual straight line. By determining the length measurement direction based on the design data in this way, it becomes possible to determine the length measurement direction in an undifferentiated way without regard to SEM edge to be formed.

Embodiment 4

As previously stated in Embodiment 3, the same type of semiconductor circuit elements include those which are important as evaluation objects and the others that are not so important. From the viewpoint of measurement accuracy also, the important evaluation objects must be measured with high accuracy whereas the evaluation objects that are low in importance are measurable with relatively low accuracy.

In cases where the length measurement value of a pattern is greatly changed from the size value of design data, it is considered that there is a sort of problem in process or in pattern design at there. In order to inquire into this problem, EPE measurement is carried out; however, in case a difference between the design data size value and the pattern's length measurement value falls within a range of preset allowable error, it is desirable to judge that the pattern is formed properly from the viewpoint of length measurement efficiency.

In this example, a technique is proposed for varying the allowable error range in accordance with the importance of an object being measured to thereby avoid unwanted decrease in evaluation accuracy or in length measurement efficiency otherwise occurring due to mere standardized determination of a length measurement error. For example, while the length measurement portion C and the length measurement portion D stated in Embodiment 3 are almost the same length measurement objects, the length measurement portion C is an important length measurement portion in light of the relationship with a pattern to be formed in the upper layer through a contact hole(s) as stated supra whereas the length measurement portion D is a pattern which is low in order of evaluation priority from the relationship with the pattern formed in the upper layer. In the case of such an example, it is recommendable to set an allowable error value less than a predetermined value to the length measurement portion C while setting to the length measurement portion D an allowable error value that is greater then that of the length measurement portion C. With this arrangement, it is possible to set the optimum allowable error values based on the relationship with a pattern which is not formed yet (the pattern to be formed in the upper layer).

By making the allowable error values variable based on the information of circuit elements obtainable from the design data in this way, it is possible to realize both the improvement of length measurement accuracy and the length measurement efficiency at a time. Additionally, it is also permissible to change the allowable error values between "part appreciably affecting the characteristics of a semiconductor circuit element" and "the remaining parts" or, alternatively, between "contact portions with another pattern (or, portions expected to come into contact therewith)" and "the other portions" as has been explained in Embodiment 3.

Embodiment 5

An explanation will next be given of an example which applies complex processing to EPE measurement results of an upper layer of semiconductor wafer and its underlying layer. Design data defines an ideal shape for a pattern. In semiconductor device manufacturing processes, conditions of fabrication apparatus are adjusted so that a pattern shape maximally approximates the design data. However, the actually formed pattern can significantly change in shape from the design data due to several factors including, but not limited to, deviation of an exposure position in photolithographic apparatus, a change in conditions of lithography apparatus such as lens heating or the like, and inappropriate reproducibility of design data shape.

Instantaneous investigation of these change factors and feedback to manufacturing conditions or else lead to decreases in development period and cost of semiconductor devices.

For that purpose, an explanation will first be given of an example which obtains from EPE measurement result of each layer a distance and overlap area between SEM edges that are connected by a contact hole(s) for performing electrical connection between layers of a semiconductor wafer.

Figure 11:
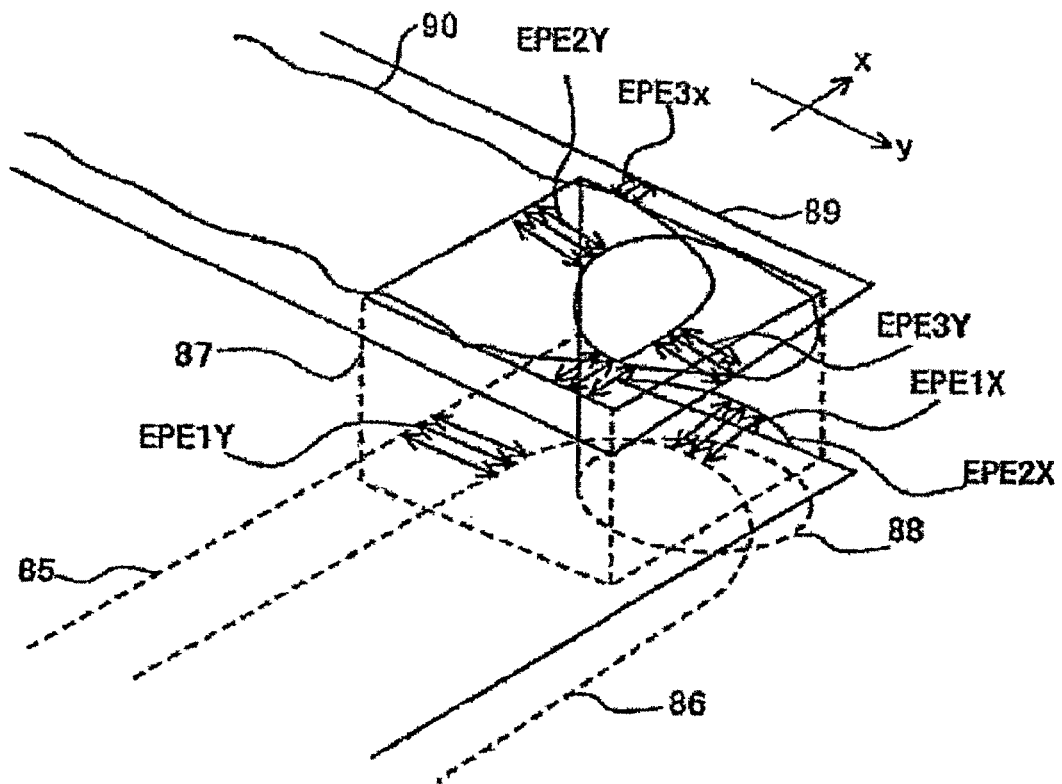
FIG. 11 is a diagram for explanation of an example which performs EPE measurement between adjacent ones of an upper wiring layer, a lower wiring layer and a contact hole for connecting together the upper and lower layers.

FIG. 11 is a diagram pictorially representing the relationship of an upper layer, a lower layer and a contact hole for connection between the upper and lower layers.

Figure 25:
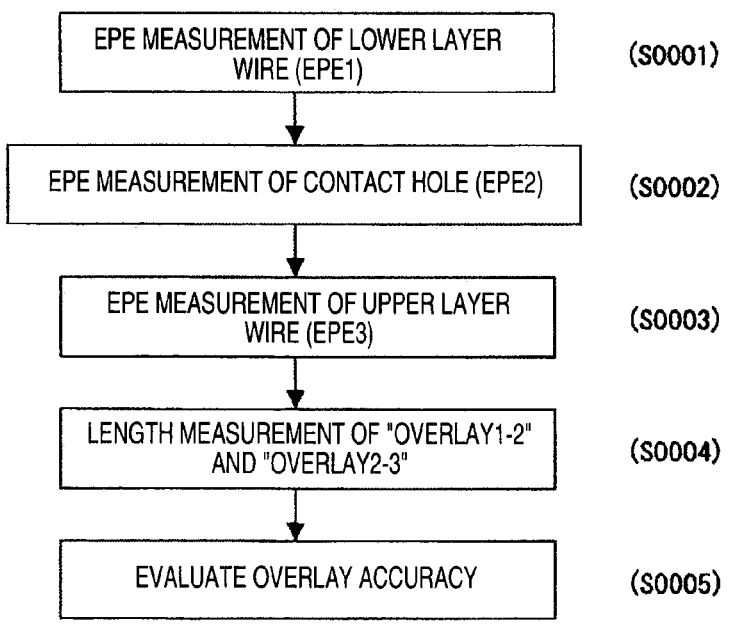
FIG. 25 is a flowchart for explanation of a process for evaluating the overlay accuracy.

As will be explained in a flow chart of FIG. 25, EPE measurement is performed between design data 85 of a lower wiring layer and a SEM edge 86 of the lower wiring layer, followed by numerical computation of EPE1 (S0001). In the case of this example, EPE measurement is performed in X direction and Y direction also; then, EPE1x and EPE1y are computed. The same goes with EPE measurement to be done later.

Similarly, EPE measurement is performed between design data 87 of a contact hole and a SEM edge 88, followed by computation of EPE2 (S0002). EPE measurement is done between design data 89 of an upper wiring layer and a SEM edge 90 for calculation of EPE3 (S0003).

Next, in order to measure the overlap (overlay) accuracy between adjacent ones of the upper layer, contact hole and lower layer, an attempt is made to obtain a length measurement value between the lower wiring layer's SEM edge 86 and the contact hole's SEM edge 88 (overlay1-2) and a length measurement value between the contact hole's SEM edge 88 and the upper wiring layer's SEM edge 90 (overlay2-3) (S0004).

In case a relative relationship between SEM edges of the upper and lower layers is judgeable from a single piece of image, the overlay1-2 and overlay2-3 are measured using such image. However, if any edge of the lower layer to be measured is not determinable, its adjacent pattern with determinability of the relative relationship of the upper and lower layers may be used to measure an overlay that is substantially equivalent to the intended one.

Based on the length measurement value obtained in this way, calculation is performed using Equations (1) and (2) below (S0005).

$$X: EPE1x + overlay1\text{-}2x + EPE2x + overlay2\text{-}3x + EPE3x \leq Thx \quad (1)$$

$$Y: EPE1y + overlay1\text{-}2y + EPE2y + overlay2\text{-}3y + EPE3y \leq Thy \quad (2)$$

Performing the above-stated evaluation makes it possible to evaluate the accuracy of superposition between the patterns of upper and lower layers connected together by a contact hole(s). The value "Thx" and "Thy" are threshold levels to be determined based on allowable values in X and Y directions, which should be determined depending on the degree of overlay that is needed to exert desired semiconductor device performance.

Embodiment 6

An explanation will next be given of an evaluation method and apparatus for evaluating a pattern that is formed by photolithographic apparatus (e.g., stepper) using EPE measurement results.

Figure 12A:
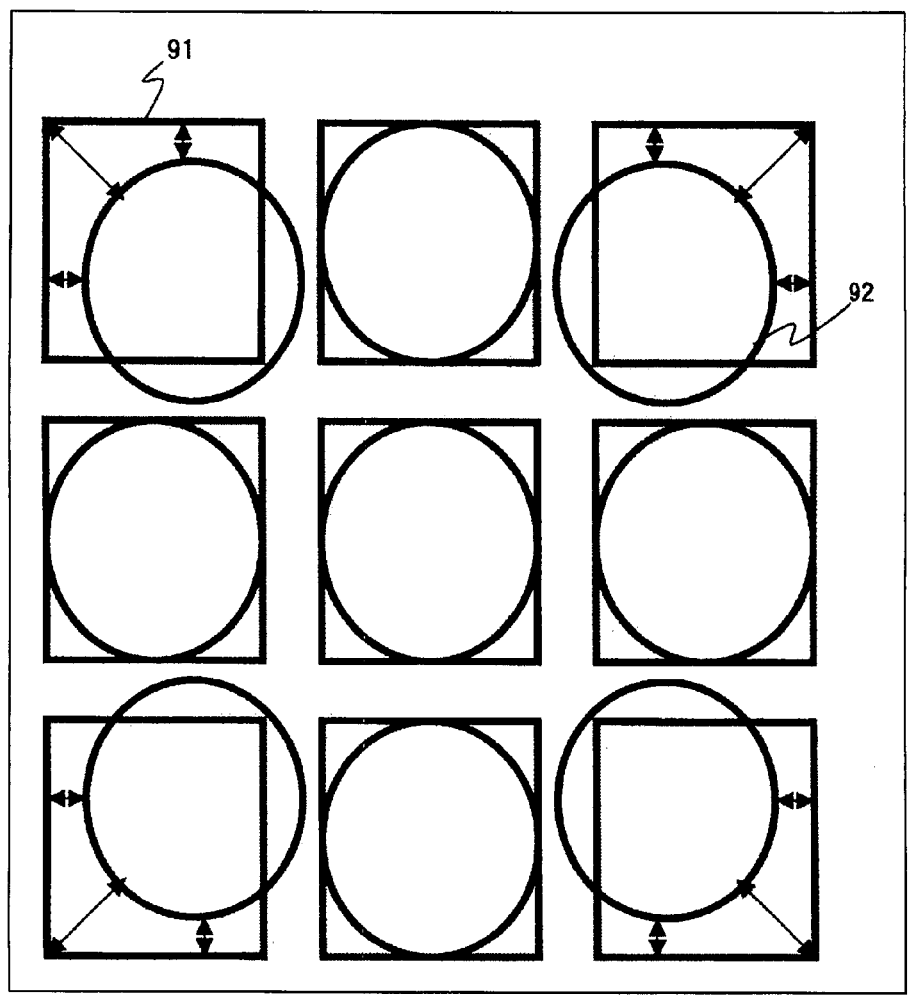
FIGS. 12A and 12B are diagrams for explanation of an example which superposes design data and a SEM edge(s) with respect to a region in which more than two contact holes are formed.
Figure 12B:
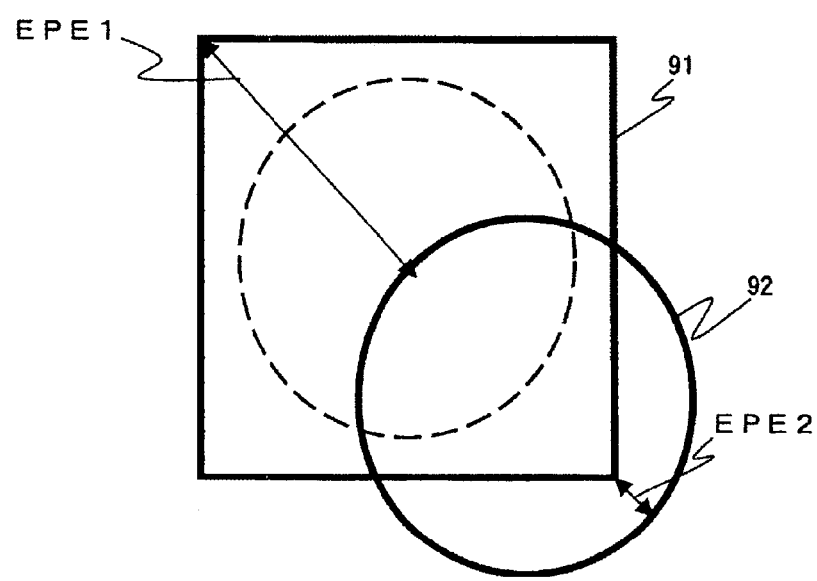

FIG. 12A is a diagram showing an example which lays a SEM edge 92 over design data 91 with respect to a region in which a plurality of contact holes are formed. FIG. 12B is its enlarged partial view. In this example, although an explanation will be given of an example which performs EPE measurement between a single SEM image which was acquired in a field view that contains nine (9) contact holes and design data corresponding thereto, this is not an exclusive one and may alternatively be arranged so that a plurality of images each including one contact hole are acquired in units of different contact holes for comparison with respective design data.

Below is an explanation of an example which evaluates the exposure accuracy of a light projection lithography apparatus (stepper) for transferring a pattern onto a semiconductor wafer.

As shown in FIGS. 12A-12B, when performing EPE measurement in units of prespecified regions, an EPE measurement result of a hole pattern has certain tendency in some cases. In the case of the example of FIGS. 12A-12B, peripheral holes are formed so that these are wholly shifted in position toward the center. In case such tendency is found within a one shot of the stepper for example, it is considered that the stepper's lens is defective, resulting in the presence of an error in projection magnification. In addition, by performing EPE measurement for a plurality of patterns within one shot, it is possible to judge which one of the design data per se or the exposure condition is faced with problems.

Figure 24:
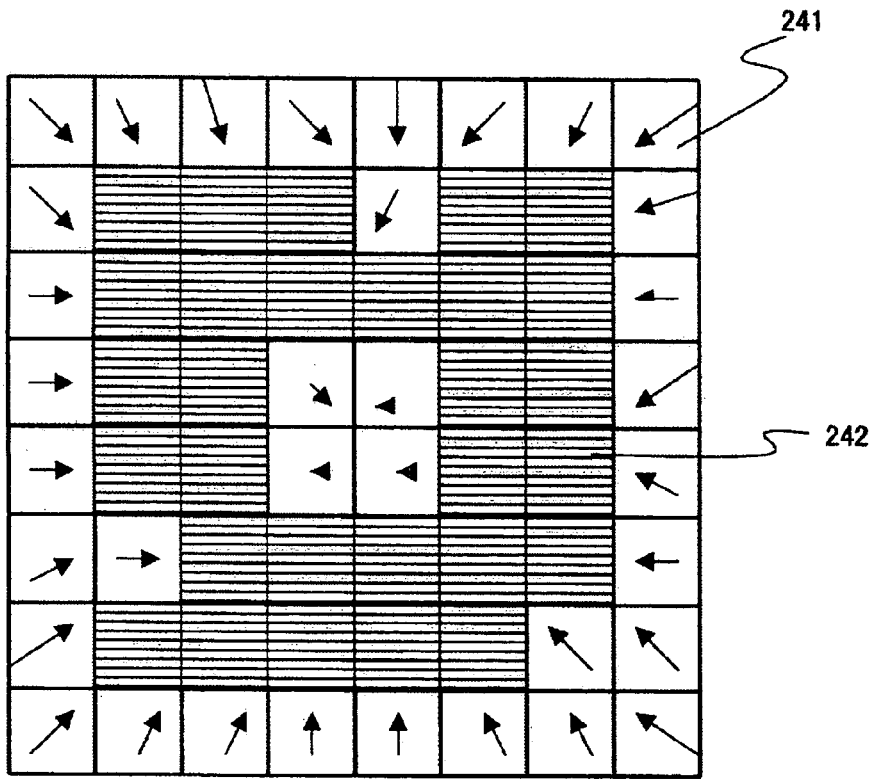
FIG. 24 is a diagram for explanation of an example for visually displaying EPE measurement results in a map form per prespecified unit area.

Further, as shown in FIG. 24, it becomes possible by displaying EPE measurement result in a map form on a per-region basis to visually affirm the tendency of SEM edge offset in units of shots, for example. It displays how much the pattern is deviated in which direction with respect to each specified region. To this end, EPE measurement is executed per specified region 241 to thereby measure the offset of pattern. More specifically, by performing EPE measurement between SEM edge and design data in all directions, the SEM edge's offset direction and offset amount are detected based on a distance between the design data and SEM edge that is furthest from the design data.

In the case of this example, computation is done to define EPE1−{(Ld−De}/2}, where Ld is the distance of diagonal line of design data, and De is the diameter of SEM edge. By doing so, the true offset amount is obtained, from which excluded is a size change corresponding to a scale-down amount of SEM edge with respect to the design data, wherein a direction indicating the largest value in this offset amount is defined as the offset direction. Other techniques may be used if such offset direction is well specifiable.

Although the example stated above is such that the direction of EPE measurement is set with design data being as a reference, this is not restrictive of the invention and may be modified so that the EPE measurement direction is determined on the SEM edge basis.

An arrow with its length proportional to this offset amount is displayed within each specified region 241. In case more than two EPE measurement results are present within the specified region 241, its average value may be displayed as an arrow; alternatively, a value obtainable based on an EPE measurement result of a specific pattern may be displayed as the arrow.

Regions 242 of FIG. 24 are the areas in which EPE measurement is not performed yet. Displaying with such identifiability in this way makes it easier to judge whether the length measurement has been performed or not.

In addition, by selectively displaying the regions 241 indicative of the presence of an offset more than a prespecified value or alternatively by distinguishably displaying the other regions, it is possible to extract and display certain portions with excessively large offset amounts. Thus it becomes possible to visually affirm the inplane tendency within a specified on-device region (e.g., the entirety of wafer).

Figure 28A:
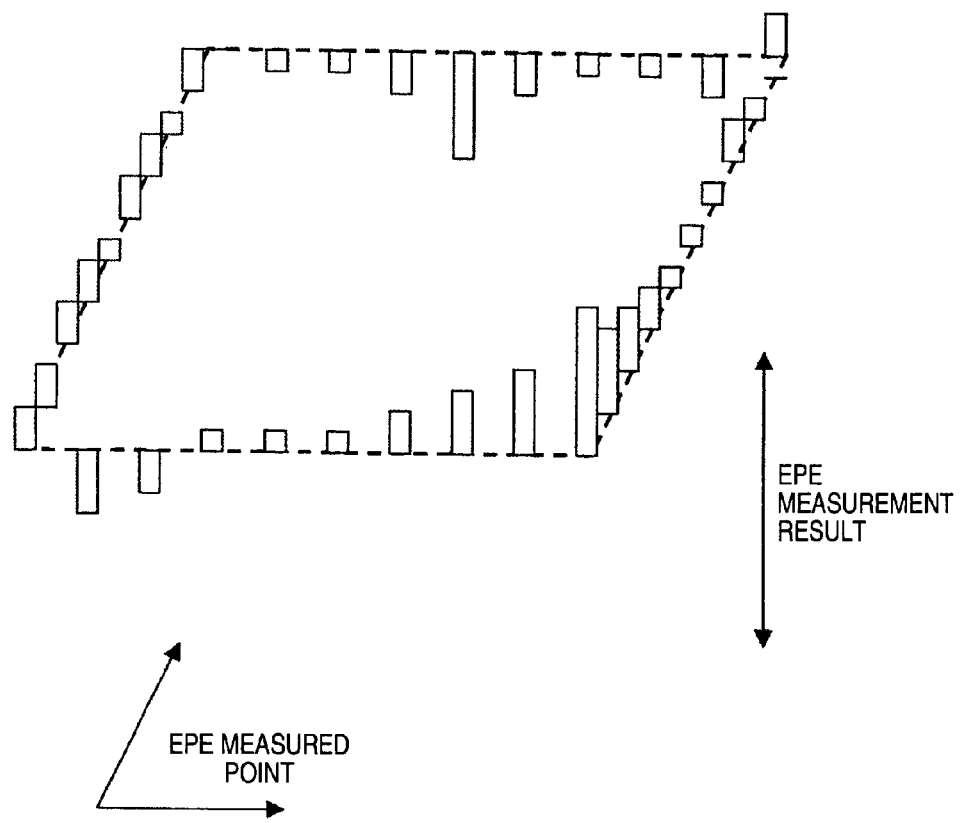
FIGS. 28A and 28B are diagrams each showing an exemplary three-dimensional (3D) display image of EPE measurement result.

A further modification is that all-direction EPE measurement is performed with respect to SEM edge 92 and displayed in a three-dimensional (3D) fashion as shown in FIG. 28A. In the case of this example, the vertical axis of FIG. 28A indicates the EPE measurement results whereas the transverse axis indicates either EPE measurement locations or direction thereof.

Figure 28B:
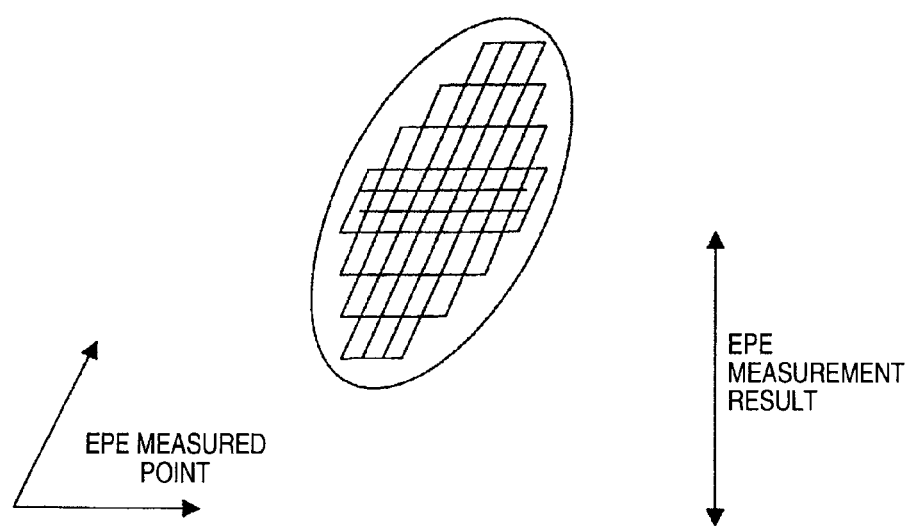

Additionally, by 3D displaying all-direction EPE measurement results in the form of a wafer map as shown in FIG. 28B, it becomes possible to visually judge the average deviation within each chip or each shot. Note that the forms shown in FIGS. 28A-28B are not exclusively limited ones, and various kinds of display forms are selectable as far as these are capable of expressing the deviation of each chip or shot in the wafer surface direction.

It is acceptable to display the EPE measurement results in a mere wafer map style as stated supra or, alternatively, display either offset components with a scale-reduced version of pattern being excluded therefrom or a scale-down version of the pattern with pattern offset components excluded therefrom. With the displaying schemes, it becomes possible for the operator to evaluate EPE measurement results in units of SEM edge change factors relative to the design data.

Embodiment 7

An explanation will next be given, using some drawings, of an example which calculates EPE measurement results of a target layer and another layer in 2D directions (X and Y directions) to thereby measure the accuracy of overlap or overlay between layers.

Figure 13:
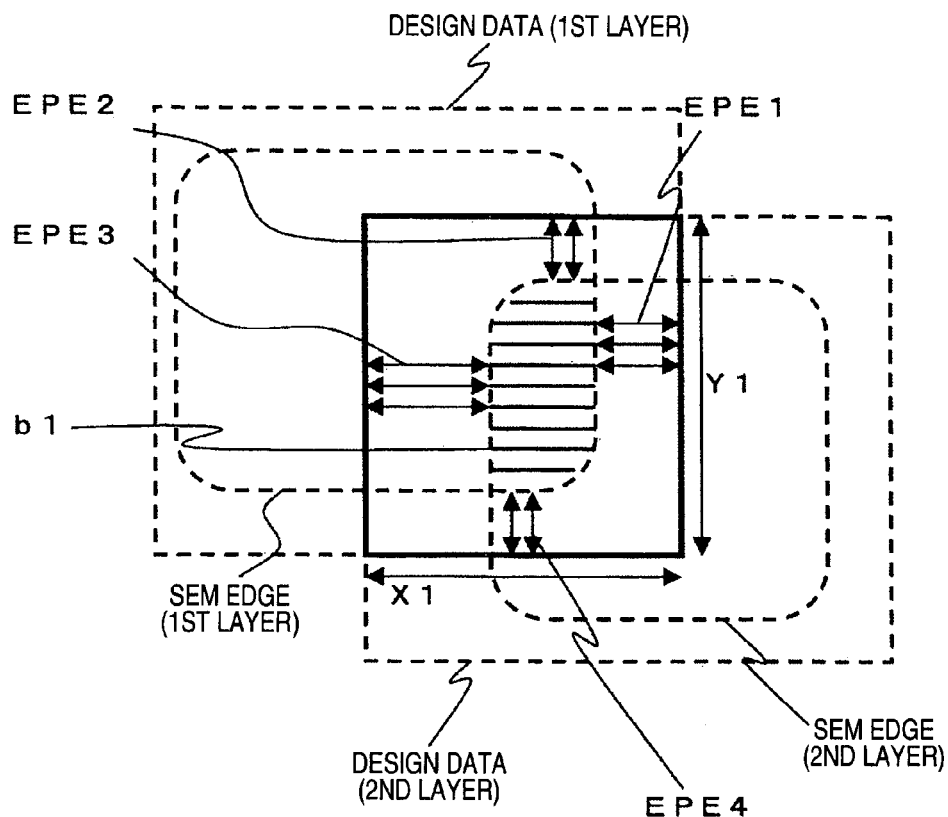
FIG. 13 is a diagram showing an example which lay over each other the design data of a semiconductor circuit element with two patterns multilayered and a SEM edge.

FIG. 13 is a diagram showing an example which lays over each other the design data of a semiconductor circuit element and a multilayer of two patterns and a SEM edge. In the case of this example, the explanation assumes that a ratio of the size of an overlapping area of two patterns in the design data versus the size of an overlay region of two patterns at SEM edge is defined as interlayer overlap accuracy. More specifically, the accuracy is evaluated under an assumption that the overlap accuracy is maximal when the ratio of a region a1 (X1×Y1) and a region b1 in FIG. 13 is 1:1.

Figure 14:
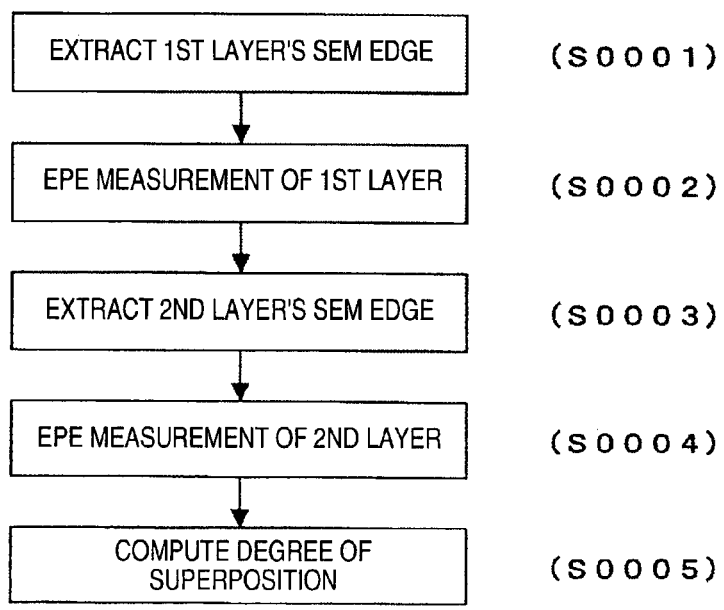
FIG. 14 is a flowchart showing a step of detecting superposition accuracy.

FIG. 14 is a flowchart showing a series of steps for detecting the overlap accuracy. First, SEM edge of a first layer is extracted from a SEM image (S0001). Then, EPE measurement is performed for the first layer (S0002). In the case of this example, length measurement of EPE1, EPE4 is performed relative to X and Y directions, respectively (S0003). Next, EPE measurement is performed for a second layer (S0004). For the second layer also, measurement of EPE2, EPE3 is performed in X and Y directions, respectively, in a similar way to the first layer.

In the case of this example, under an assumption that an overlapped portion of SEM edge has a rectangular shape, the overlap region b1 between SEM edges is calculated by: b1=(X1−EPE1−EPE3)×(Y1−EPE2−EPE4). X1 and Y1 are introducible based on design data. Then, in order to determine the degree of overlapping, b1/a1 is calculated (a1=X1×Y1) (S0005). With this scheme, it becomes possible to obtain a value(s) used to perform objective evaluation of the degree of overlay accuracy with which a real pattern is overlapped against the superposition of an ideal pattern defined by the design data.

For the first layer, after having performed matching of layout data and SEM edge, the overlay accuracy of the second layer with the first layer being as a reference, thereby making it possible to obtain the degree of overlap of the second layer with the first layer as a reference. Further, when performing the matching in the form of the first and second layers being combined together, it is possible to obtain relative overlap degree of the first and second layers. Alternatively, an attempt may be made to calculate the degree of an overlap error by computing a1/b1 in place of the b1/a1 stated above.

Although in the above-stated example the ratio of two areas is calculated to obtain either the degree of superposition or the overlapping error, this is not an exclusively limited one and may be modified, for example, to obtain an overlap degree or a degree of deviation (error) in one direction, i.e., X or Y direction.

Embodiment 8

Figure 15:
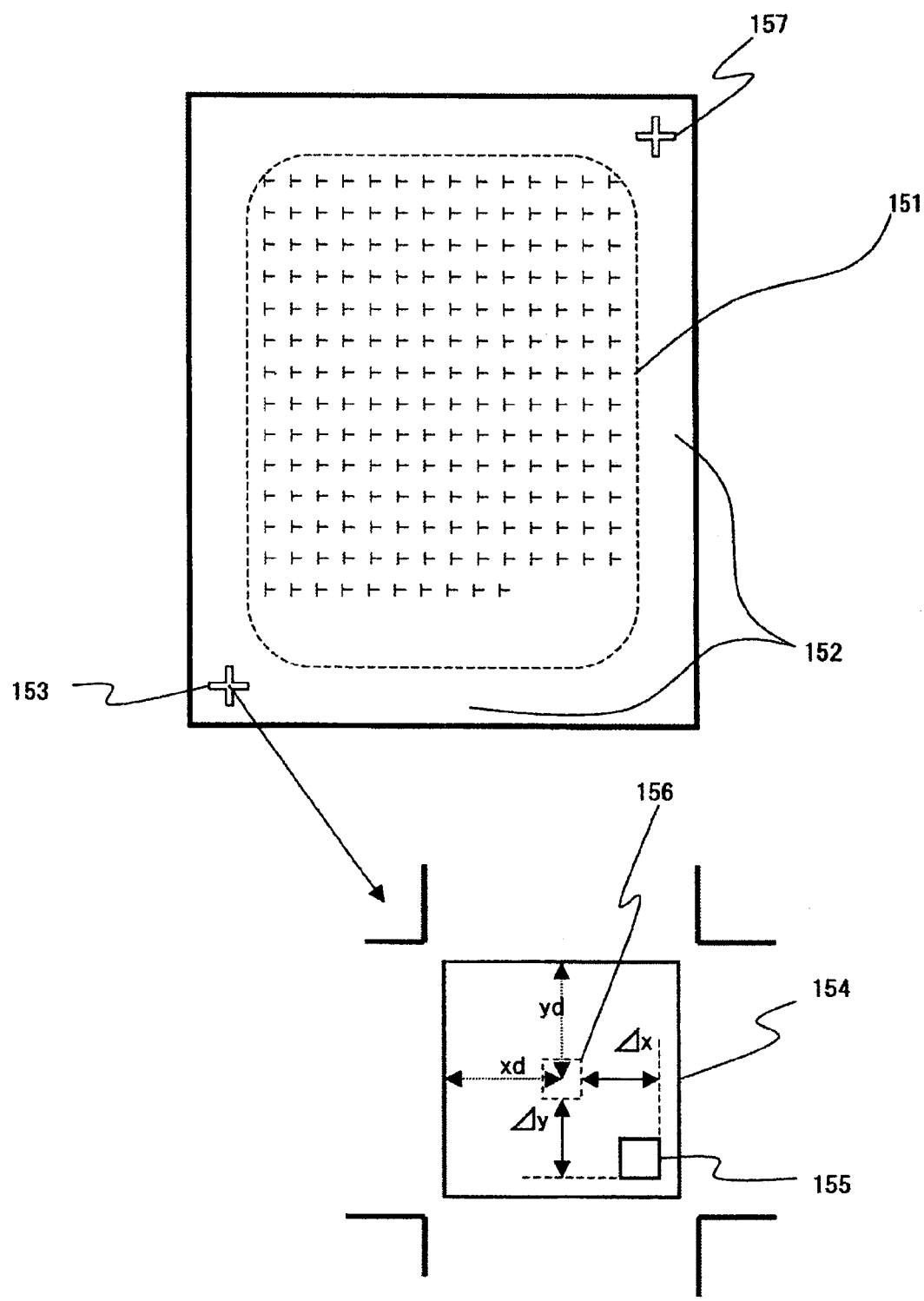
FIG. 15 is a diagram showing one example of a chip with patterns being formed through exposure by a semiconductor photolithographic apparatus.

FIG. 15 is a diagram showing one example of a chip which is exposed by a semiconductor photolithography apparatus (stepper) so that a pattern is formed thereon. This chip has a surface which is divided into two major areas: a core area 151 in which semiconductor patterns are formed, and a scribe area 152 which becomes a cutting margin during per-chip dicing. In this example, an explanation will be given of an example which implements high-accuracy EPE measurement within the core area 151 by providing an alignment mark 153 and then measuring the accuracy of superposition of an overlay measurement-use mark that is provided in the alignment mark 153.

Figure 26:
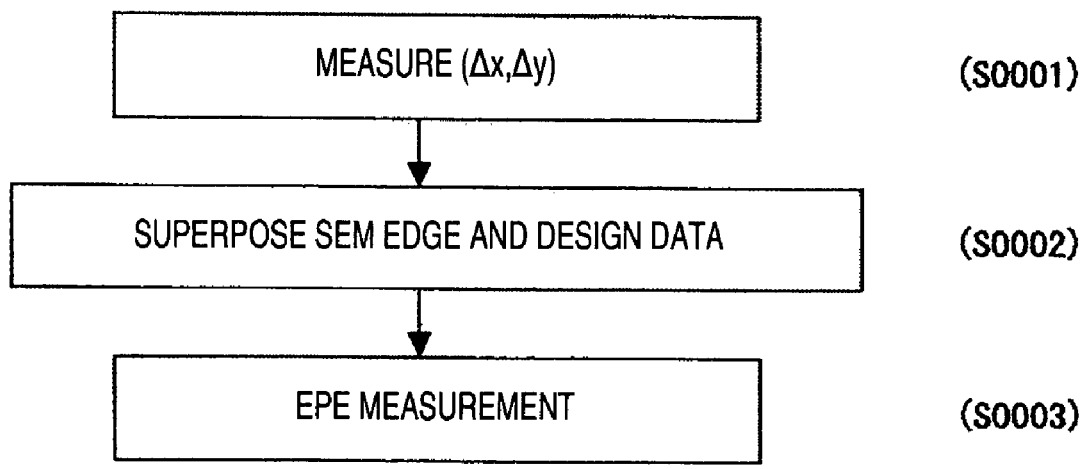
FIG. 26 is a flowchart showing one example of EPE measurement process.

FIG. 26 is a flowchart showing one example of a process of EPE measurement based on the overlay accuracy measurement. First, the overlay accuracy is measured. In this example, as shown in FIG. 15, in order to measure the overlay accuracy of the lower layer and upper layer of a semiconductor circuit element, an opening 154 is provided in an upper layer so that it extends to reach a lower layer, with a pattern 155 being provided in the lower layer to enable identification of a relative relationship with the upper layer. In this example, an explanation will be given of an example having the upper layer which is formed while being deviated or offset by $\Delta x$, $\Delta y$ from the pattern 155's ideal formation position 156.

Note that the pattern shape may be any given one as far as a relative distance between the upper and lower layers is identifiable. At step S0001 of FIG. 26, the relative relationship of the ideal pattern formation position 156 and a really formed pattern 155 is measured by SEM equipment to thereby detect a deviation of the upper layer relative to the lower layer.

The explanation here is directed to an example in which the ideal formation position 156 exists at the center position of the opening 154. In other words, the example to be explained below is such that a pattern is ideally formed to be spaced apart from a detected SEM edge of the opening 154 by a distance of (xd, yd). A relationship of the opening 154 and ideal pattern formation position 156 are registered in advance in the design data.

At step S0002 of FIG. 26, processing is performed to lay over each other the SEM edge in core area 151 and the design data while keeping an offset corresponding to a deviation ($\Delta x$, $\Delta y$) between the upper layer and lower layer thus detected at step S0001. In this case, the design data is overlaid in the state that the design data is offset from a predetermined position by the ($\Delta$x, $\Delta$y).

At step S0003, EPE measurement is performed between line segments of a pattern edge on the design data-overlaid SEM image and design data corresponding to this edge.

An EPE measurement result obtained in this way indicates a difference between a pattern position in the case of the exposure position being at a proper position and an actual pattern position. The operator can recognize the exposure state in an offset-free state even when an exposure position deviation exists; thus, even if there are more than two exposure accuracy deterioration factors including the exposure position deviation for example, discrimination is enabled on a per-factor basis, thereby making it possible to facilitate early finding of proper exposure conditions.

More practically, in the case of EPE measurement being performed about a plurality of patterns within the core area 151, some patterns can sometimes exhibit a difference from the others in EPE measurement result. In this case, it is also considered that a per-shot exposure position deviation and pattern position deviation based on other factors are included therein, so mere execution of EPE measurement would result in the lack of an ability to concretely figure out the exact position deviation factor.

By performing EPE measurement in the state that per-shot exposure position deviation is corrected as in this example, it becomes possible to make easier concrete grasp of the factor or cause other than exposure position deviations.

Although in this example the explanation is directed to one specific example which corrects a deviation amount detected and lays the design data and SEM edge over each other, this is not a restrictive one, and another technique is also employable for performing EPE measurement between the superposed design data and SEM edge without performing correction and, thereafter, subtracting ($\Delta$x, $\Delta$y) therefrom.

It is also possible to specify rotation components of the whole exposure region by evaluation of a deviation between the upper layer and lower layer of another alignment mark 157. Thus it becomes possible to evaluate such exposure position deviation in x and y directions and also in R direction.

Additionally, deviation of the alignment mark 153 that is provided in the scribe area 152 with respect to the lower layer indicates an entire exposure position offset of a single shot of the photolithographic tool. By comparing this deviation (or the degree of coincidence between the upper layer and lower layer) to the average EPE measurement result within the core area 151, it is possible to perform calibration and reliability analysis of alignment marks. More specifically, the above-noted object is attainable by calculating a difference or ratio of the deviation of overlay mark (offset of the upper layer relative to the lower layer) and the average value of EPE measurement results of more than two patterns in the core area and then evaluating a resultant value.

Embodiment 9

Figure 16:
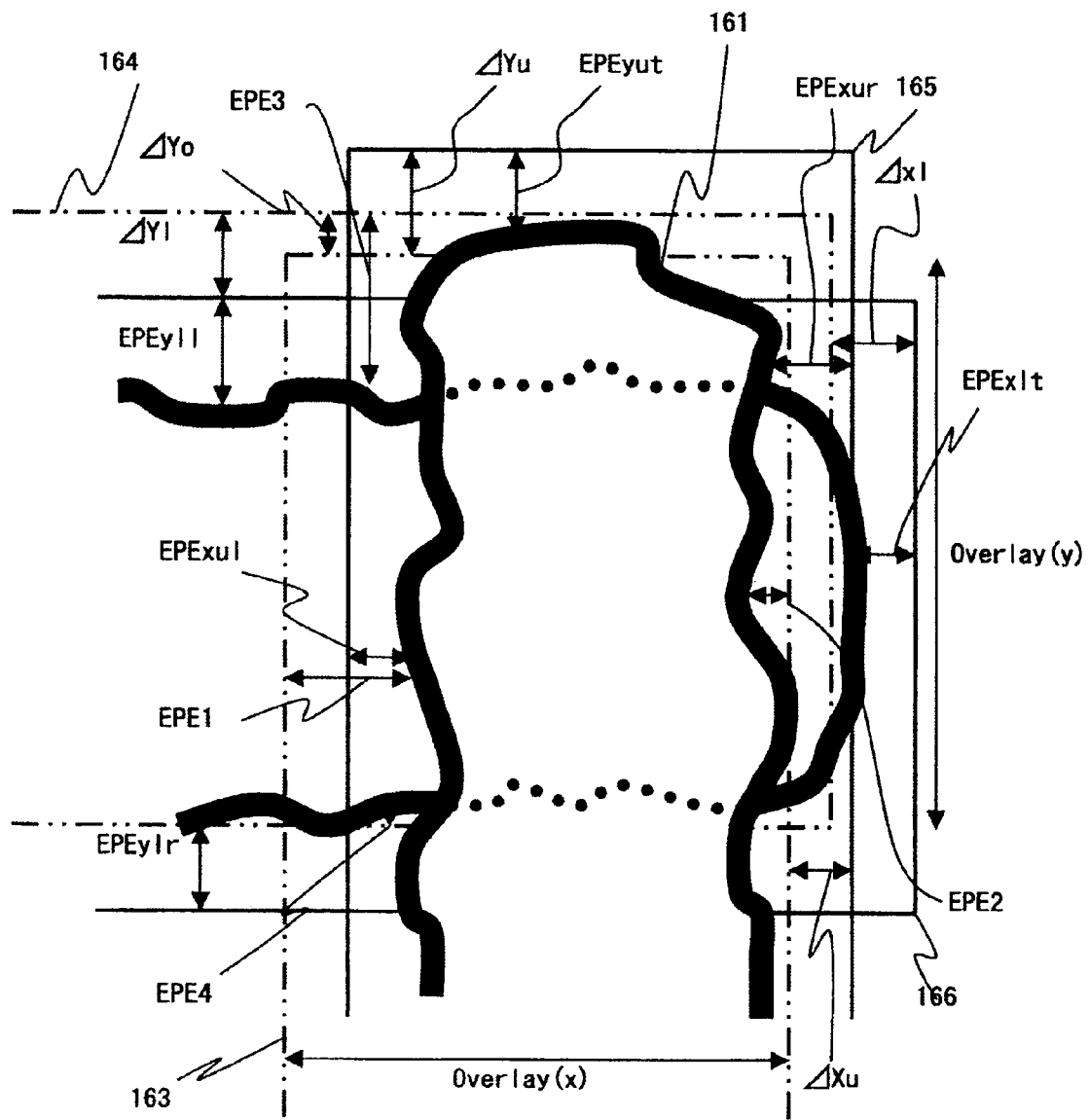
FIG. 16 is a diagram for explanation of an example which measures the overlay accuracy between a pattern formed at upper layer part and a pattern formed at lower layer part.

FIG. 16 is a diagram for explanation of an example which measures the accuracy of overlay between a pattern that is formed in an upper layer portion (SEM edge 161 of upper layer pattern) and a pattern formed in a lower layer portion (SEM edge 162 of lower layer). In this example, there will be described a technique suitable for measuring the accuracy of an overlay changing based on a deviation of SEM edge with respect to design data and a scale-reduction amount of SEM edge relative to the design data. The explanation below uses an example in which design data 164 of the lower layer pattern and a SEM edge 162 of the upper layer pattern for design data 163 of the upper layer pattern plus a SEM edge 161 of the upper layer pattern are formed as shown in FIG. 16. Although the explanation is given while supposing that the deviation of SEM edge relative to the design data is detected in case the design data and SEM image are overlapped with an alignment pattern (not shown) being as a reference, this is not to be construed as limiting the invention.

Based on the design data and SEM edge superposed, measurement is performed of an overlapping part of the upper layer pattern and the lower layer pattern. More precisely, EPE measurement is performed between the design data 164 of the lower-layer wiring line and the SEM edge 162 to thereby measure deviations EPE3 and EPE4 of from a pattern line direction to vertical direction. Similarly, EPE1 and EPE2 are measured with respect to the upper-layer wiring line.

Based on the EPE1 to EPE4 thus measured in this way, calculation is executed using Equations (3) and (4) below:

$$Xm = \text{overlay}(x) - (EPE1 + EPE2), \quad (3)$$

$$Ym = \text{overlay}(y) - \{(EPE3 - \Delta Y0) + EPE4\}. \quad (4)$$

The overlay(x) and overlay(y) indicate the sizes in x and y directions of an overlap portion of two patterns on the design data, and $\Delta Y0$ is the size of an offset between the design data 163 and design data 164, which size was originally set on the design data.

By multiplying Xm and Ym, it is possible to obtain the area of an overlap portion of SEM edge. By comparing the calculated area to the area of an overlapping part on the design data (overlay(x)×overlay(y)), it is possible to perform evaluation of the real overlay region against the ideal value.

Embodiment 10

Figure 27:
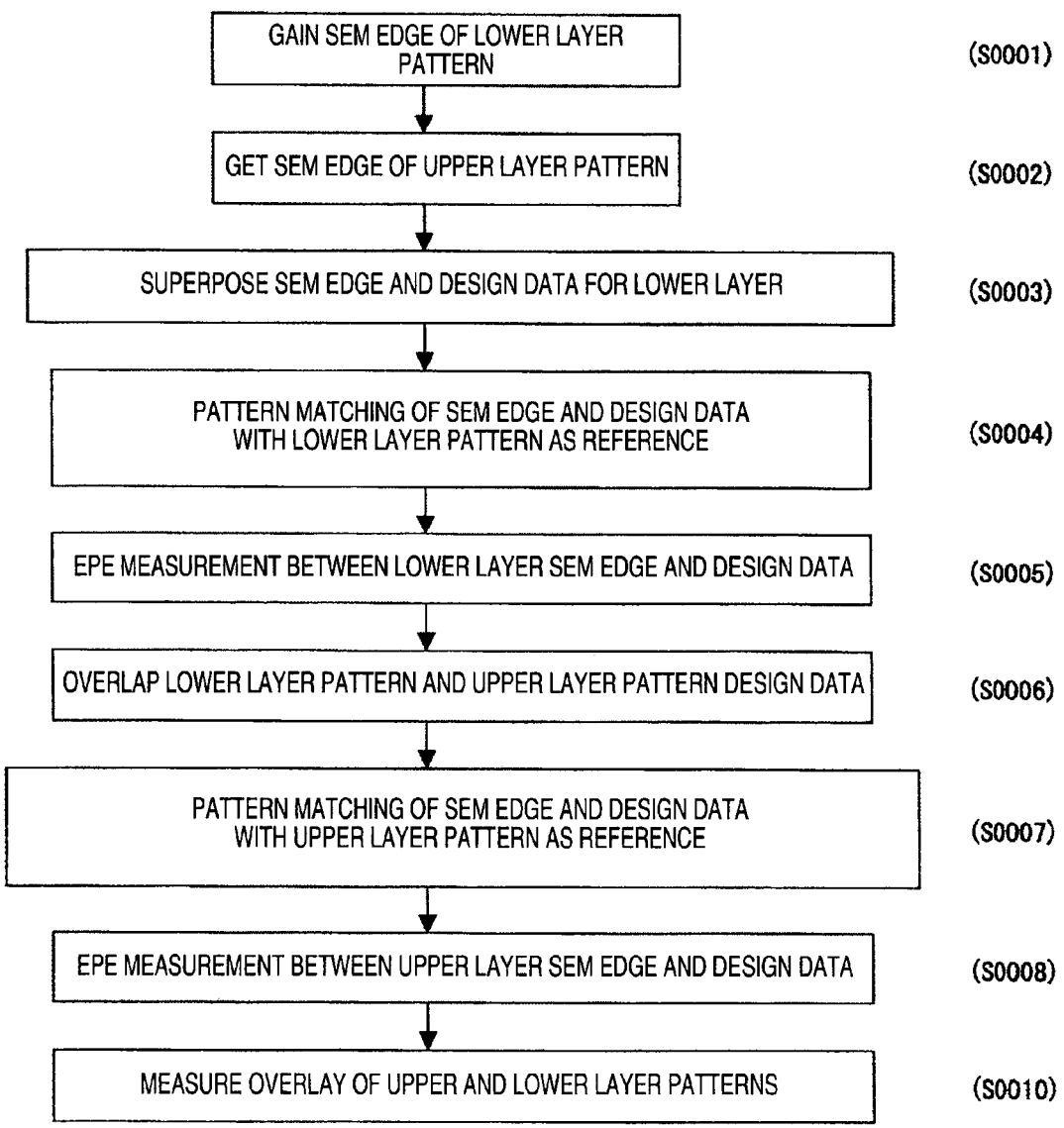
FIG. 27 is a flowchart for explanation of a process of evaluating the overlay accuracy.

While in Embodiment 9 the explanation was given under the assumption that SEM edge 161 of the upper layer pattern and SEM edge 162 of the lower layer pattern are verifiable on a single SEM image, it will possibly happen that relative relationship between the upper layer pattern and lower layer pattern is not judgeable by use of one SEM image due to the presence of a dielectric film being formed between the lower layer pattern and upper layer pattern. In this example, referring to a flowchart of FIG. 27, an explanation will be given of an example which is suitable, even in such case also, for measurement of the accuracy of an overlay between the upper layer pattern and lower layer pattern.

First, a SEM edge 162 of the lower layer pattern is acquired, and its data is stored (S0001). After having formed the upper layer pattern, SEM edge 161 of the upper layer pattern is acquired (S0002). Next, based on an alignment mark(s) not shown, superposition is performed of the SEM edge 162 of upper layer pattern and the design data 164 of lower layer pattern. In this event the superposition is done so that the alignment mark being formed on the lower layer is matched between the design data and SEM image (S0003). At this time, the superposition is performed based on a distance between the alignment mark measured at the time of SEM edge acquisition and the pattern and a distance between an alignment mark preregistered to the design data and a pattern to be measured.

Next, pattern matching is performed between the SEM edge and the design data with SEM edge 162 of lower layer pattern being as a reference (S0004). A matching shift amount obtained in this process ($\Delta$X1, $\Delta$Y1) is stored. Next, EPE measurement is performed between the pattern matching-applied SEM edge 162 of lower layer pattern and the design data 166 of lower layer pattern, thereby measuring EPEylr, EPEy1ll (S0005).

Next, let the design data 165 of upper layer pattern be superposed at a position that is deviated from the original design data position 163 by a distance corresponding to a deviation (Δxu, Δyu) of the upper layer pattern and lower layer pattern as measured using an overlay mark, not shown (S0006). Note here that in this example an explanation will be given while supposing that a deviation between the design data and SEM edge with the alignment mark as a reference is contained in (Δxu, Δyu).

Next, with the design data 165 of the upper layer pattern as a reference, pattern matching is performed between the design data 165 of upper layer pattern and the SEM edge 161 of upper layer pattern (S0007). As the above-stated (Δxu, Δyu) contains therein the relative distance of upper layer pattern and lower layer pattern and relative distance between SEM edge of upper layer pattern and design data, it becomes possible by performing pattern matching of the both to form a composite image with substantive reproducibility of the superposition of upper layer wiring line and lower layer wiring line.

Next, EPE measurement is performed between the design data 161 of upper layer pattern and SEM edge of upper layer pattern to thereby measure EPExul, EPExur (S0008). Based on the measurement values, an overlay of the lower layer wire and upper layer wire is calculated in a way which follows (S0009).

$$Xo = \text{overlay}(x) - \{\Delta Xu + \text{EPE}xul\} + \Delta xu + \text{EPE}xur\} \quad (5)$$

$$Yo = \text{overlay}(y) - \{\Delta Yl + \text{EPE}yll - Yo\} + (\Delta yl + \text{EPE}ylr\} \quad (6)$$

A product of Xo and Yo (Xo×Yo) indicates the actual overlay area. By comparing this value with an overlay area (overlay (x)×overlay (y)) on the design data, it becomes possible to evaluate the overlay accuracy.

Performing the computation makes it possible to evaluate relative relationship between the upper and lower layer wiring lines even in cases where these are failed to appear in a single piece of SEM image.

Embodiment 11

Figure 17:
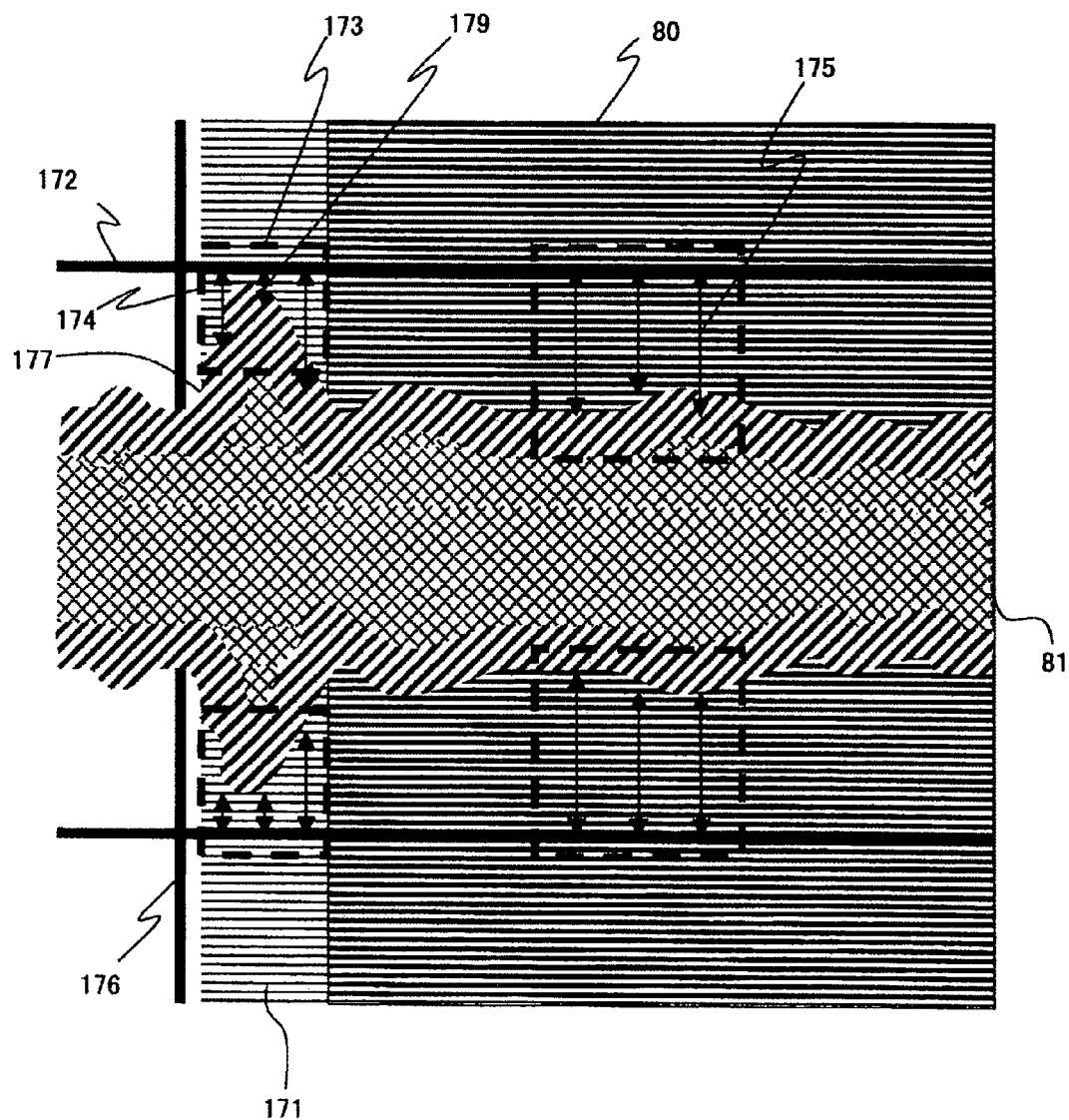
FIG. 17 is an enlarged view of a portion at which an active area and a step-like portion made of dielectric material and a gate pattern are overlapped together.

FIG. 17 is an enlarged view of a portion of the pattern of FIG. 8, at which the active area 80 and a step-like area 171 made of dielectric material plus the gate pattern 81 overlap together. The step 171 is formed in a semiconductor device manufacturing process in a way which follows: after having formed the active area 80 on a semiconductor circuit element, a dielectric layer is formed, which is selectively etched by chemical mechanical polishing (CMP) apparatus to remove unnecessary portions thereof.

As the active area 80 is formed at a lower level than its peripheral part, the dielectric material formed at the periphery of active area 80 is hardly etched away by CMP apparatus and is formed as the step 171 for retaining dielectricity between active area 80 and other regions.

However, it sometimes happens that the step 171 is overetched due to the failure to properly select CMP polishing conditions and the kind of dielectric material, resulting in a change in characteristics of a transistor that is structured by the active area 80 and gate pattern 81. Mere use of 2D SEM images poses a problem as to the difficulty in verifying whether the step 171 is formed properly or not.

In this example, in order to avoid this problem, it is proposed to perform length measurement with respect to the overlapping portion of the step 171 and gate pattern 81. In particular, if step 171 is reduced more than unnecessary, it becomes a shape with gate pattern 81 being partly projected as shown in FIG. 17. Measuring the projected part of gate pattern 81 is equivalent to evaluation of the step 81's 3D shape which caused the unwanted formation of such projected portion. Hence, according to this example, it is possible to perform evaluation in a direction along the depth of a workpiece based on the information obtained by SEM. Furthermore, it becomes possible to readily find out the proper CMP polish conditions and the appropriate kind of dielectric material.

An explanation will be given below of an example which performs EPE measurement to determine a distance between design data 172 of the gate pattern and the projected portion of gate pattern. A box cursor 173 (174) is disposed in close proximity to a position at which the gate pattern design data 172 and design data 176 of the active area are crossed together so that it is placed to overlie the step 171. Next, within the box cursor 173 (174), EPE measurement is performed between the gate pattern 81 and the gate pattern design data 172. Length measurement is done with respect to more than one measuring point in such a way as to determine the length of a projected portion 177 of the gate pattern 81.

Although this example is arranged so that the length of projected portion 177 is evaluated by length measurement of the distance between a tip end of the projected portion 177 and the design data 172 of gate pattern, this is not restrictive of the invention. Another exemplary technique is employable for subtracting the length measurement value of a length measured portion 179 within the box cursor 173 from the length measurement value of a length measured portion 175 within a box cursor 178 that is assigned to another length measured location of the gate pattern 81 to thereby obtain the length measurement value of the projected portion 177.

The length measurement value thus measured in this way is stored as the length measurement value of the step part while being distinguished from the length measurement portion 175 of another gate pattern, by way of example. The operator is capable of performing, based on the length measurement value thus measured in this way, evaluation of the CMP polish conditions and the kind of the dielectric material. If the projected portion 177 is too large, it is considered that there must be a serious problem(s) in the semiconductor device fabrication process. Accordingly, an arrangement may also be employed for generating, when the EPE measurement result of the projected portion 177 goes beyond a predetermined threshold value, an error signal for notifying the operator of such situation.

Even when the projected portion 177 is large, if other measured portions 175 of the gate pattern are large similarly, it is very likely that such is not the problem of CMP polish conditions. Consequently, it is also permissible to employ an arrangement which performs length measurement of the other length measurement portions 175 of the gate pattern together with the length measurement result of the projected portion 177 and which changes a message for the operator between when the ratio of the both exceeds a prespecified significance and when it is less than the prespecified significance.

Furthermore, by displaying in a wafer map form the length measurement results in units of chips of a semiconductor wafer or in units of predetermined regions, it becomes possible to specify more definitely the reason why the projected portion 177 is formed.

For example, in the event that the projected portion 177 is largely formed to span the entire wafer surface, CMP polishing is excessive in some cases, and the dielectric material used is problematic in composition in other cases. Alternatively, in case the large projected portion 177 is formed with deviation toward a partial region of the wafer, it is believed that the wafer is warped with or without a CMP-use polish pad being wore out unevenly. In case similar length measurement results are detected concentrically also, it is considered that the polish pad per se has defects.

When forming the wafer map, either one length measurement result or an average value of more than two length measurement results is distinguishably displayed on a per-chip basis or in units of prespecified regions while dividing it into length measurement result groups each covering a predetermined range. This makes it possible for the operator to visually judge the tendency of the whole wafer.

Embodiment 12

Figure 18:
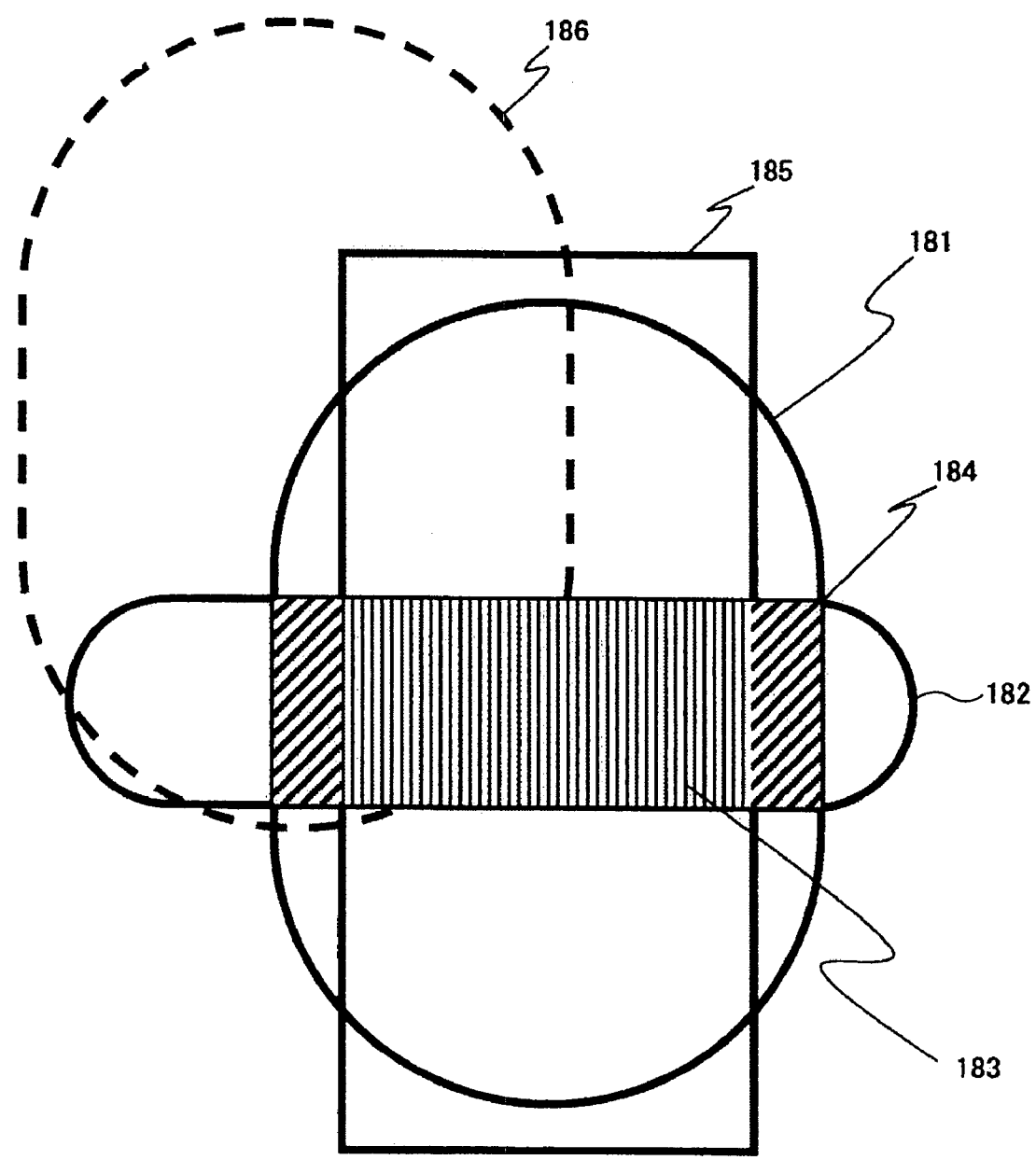
FIG. 18 is a diagram for explanation of a technique suitably adaptable for evaluation of a transistor to be formed by laying the gate pattern over the active area.

FIG. 18 is a diagram for explanation of a preferred technique for evaluating a transistor to be formed by laying a gate pattern 182 over an active area 181. In this example, in particular, an example will be explained which performs evaluation of the transistor by comparing an actually formed transistor region 184 (transistor region to be specified by SEM edge) to an ideal transistor shape on design data 183 of the active area.

Firstly, a SEM image is formed, from which an overlapping region of the active area 181 of SEM edge and the gate pattern 182 of SEM edge is extracted as a real transistor region 183. Next, pattern matching is performed between the design data 185 of the active area and the SEM edge 181 of active area, thereby performing position alignment therebetween.

In the state that the position alignment was done, the overlap region of the active area design data 185 and SEM edge 182 of the gate pattern is the transistor region 183 on the design data to be formed when the active area is properly formed in a way suggested by the design data. An area or lengths in X and Y directions of the transistor region on the design data is/are measured by EPE measurement or image processing or else; then, based on its result, comparison is performed between the transistor region 184 on a real image and the transistor region 183 on the design data. With this comparison, it is possible to evaluate the performance of actual transistor relative to the ideal transistor on the design data. This makes it possible to evaluate the semiconductor device fabrication process of interest.

As shown in an active area 186 formed by dotted lines, even if the active area is not positioned at an ideal position, a characteristic of a transistor can be evaluated by evaluating an area overlapping with a gate pattern.

The transistor evaluation is achievable by using any kinds of parameters that permit relative evaluation between the both, such as a difference in transistor length in one direction or in area, a ratio and other similar suitable ones.

Figure 19:
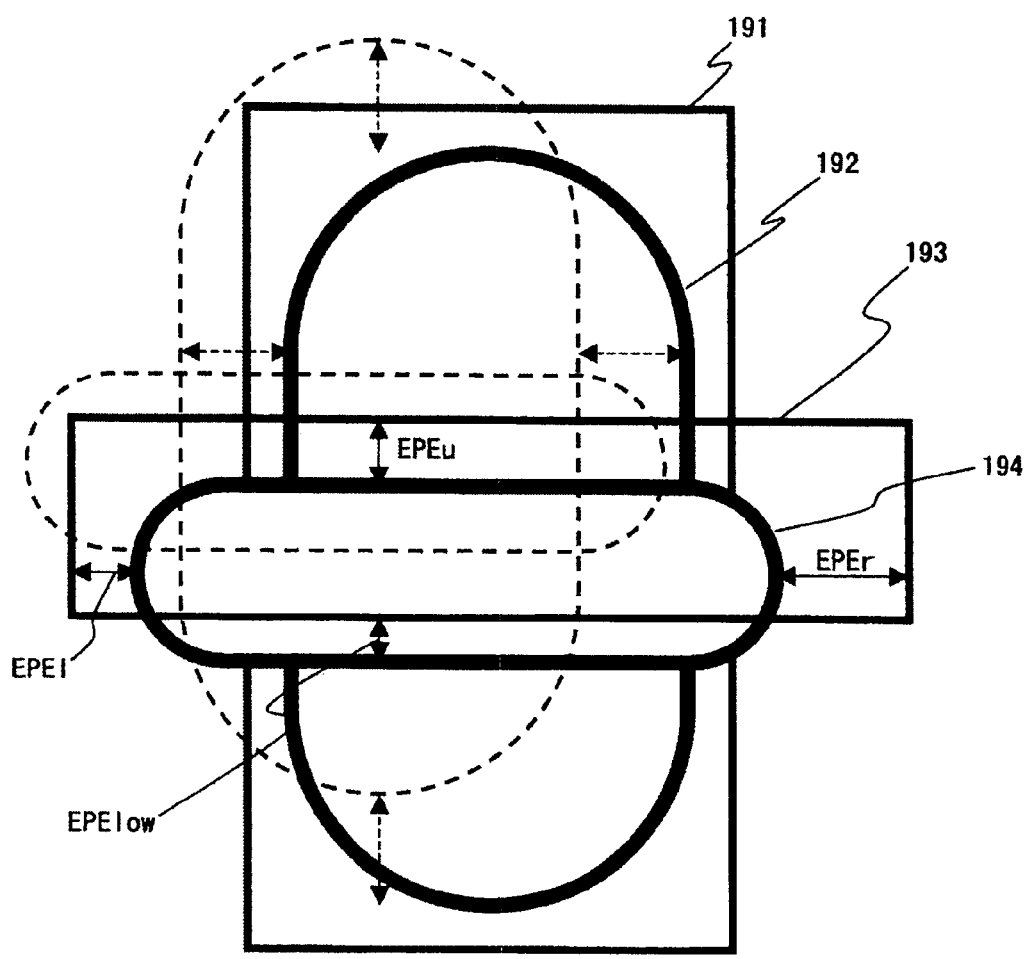
FIG. 19 is a diagram for explanation of an example which performs EPE measurement between a gate pattern on design data and a gate pattern of SEM edge.

FIG. 19 is a diagram showing an example which performs the matching of design data 191 of an active area and SEM edge 192 of the active area and then performs EPE measurement between a gate pattern 193 on design data and a gate pattern of SEM edge.

The EPE measurement result (EPEu, EPElow, EPEr, EPEl) obtained after having performed the matching between both active areas is the one that indicates a degree of deviation of both patterns from the ideal relative position relationship of the active area and gate pattern. By performing EPE measurement through this process step, it is possible to perform the intended transistor performance evaluation irrespective of any positional deviation of the entirety of pattern.

Figure 20:
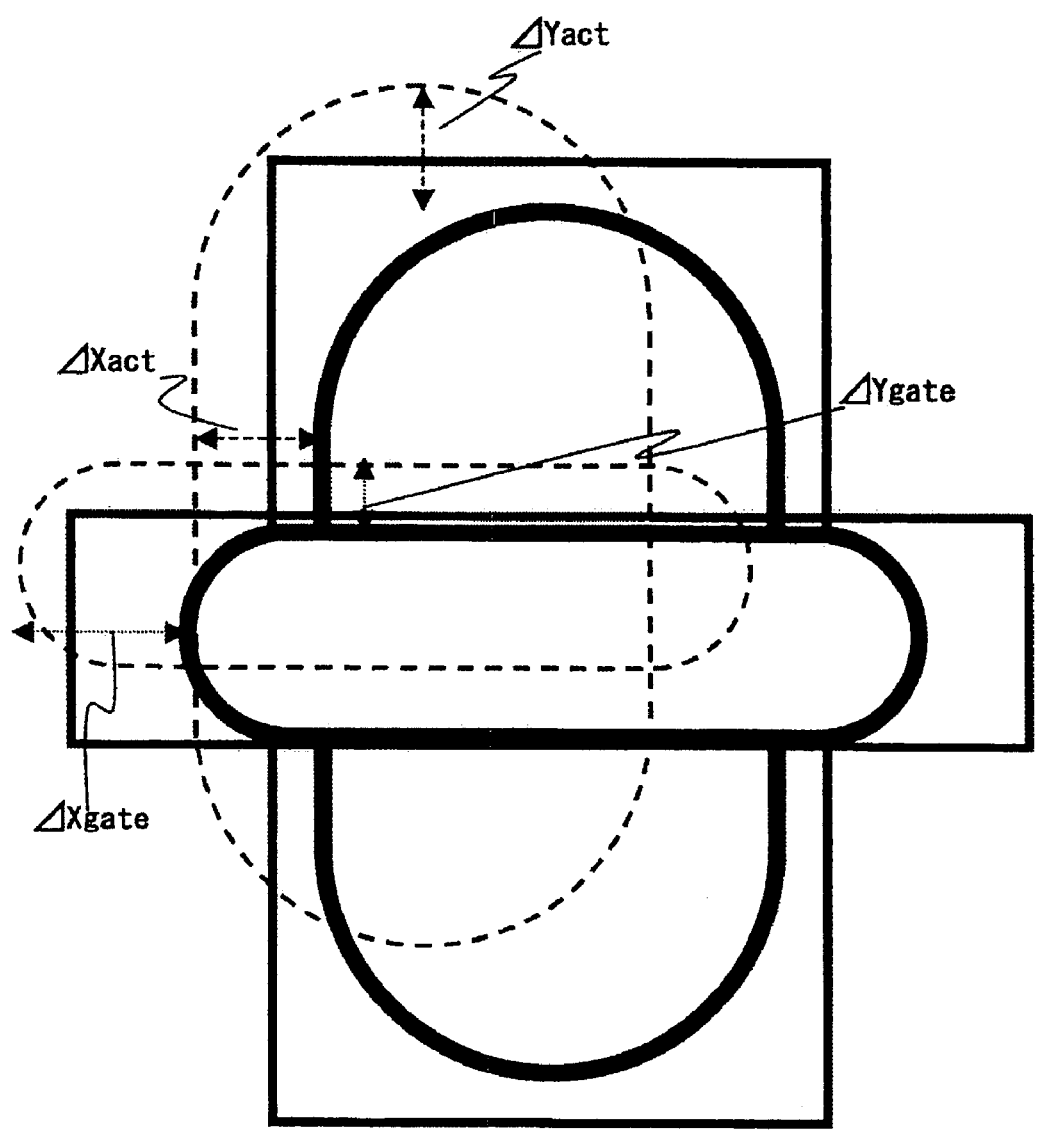
FIG. 20 is a diagram for explanation of an example which measures the overlay accuracy between the active area and gate pattern.

FIG. 20 is a diagram showing an example which performs matching separately for an active area and for a gate pattern to thereby measure the degree of overlapping of the both (i.e., overlay accuracy) based on a shift amount obtained. A matching amount of the active area is given as ($\Delta$Xact,$\Delta$Yact) whereas the gate pattern's matching amount is ($\Delta$Xgate,$\Delta$Ygate). A difference between these shift amounts ($\Delta$Xact–$\Delta$Xgate,$\Delta$Yact–$\Delta$Ygate) becomes a parameter indicative of the overlay accuracy. If no such shift amount difference is found, at least the relative relationship of the gate pattern and active area is identical to the design data. According to this example, evaluating the difference between two shift amounts makes it possible to accurately measure the overlay accuracy without being affected by the deviation in position of the formed pattern per se.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A pattern length measurement method for laying over each other design data of a pattern under inspection of a semiconductor integrated circuit and image data of the pattern under inspection to measure a length between a pattern edge of the design data and a pattern edge of the image data, the method, using a processor, to perform the following steps:
    acquiring the image data of a region containing the pattern;
    measuring a length of length measurement points at different positions between a pattern edge of the image data and a contour corresponding to an (other) edge obtained based on the design data;
    categorizing length measurement results of the length measurement points into predetermined region units; and
    performing a statistical processing of the length measurement results of the measurement points at the different positions to evaluate the length measurement results for each of the categorized units of the measurement results.

2. The pattern length measurement method according to claim 1,
    wherein the statistical processing includes an average value calculation of the length measurement results.

3. The pattern length measurement method according to claim 1, further comprising:
    determining an allowable error value of length measurement result with respect to each length measurement result group categorized.

4. A pattern length measurement method for comparing design data of a pattern under inspection of a semiconductor integrated circuit and image data of the pattern under inspection to measure a length between a pattern edge of the design data and a pattern edge of the image data, the method, using a processor, to perform the following steps:
    acquiring the image data of a region including the pattern;
    measuring a length of length measurement points at different positions between the pattern edge of the image data and a counter corresponding to an (other) edge obtained based on the design data for each of a pattern of one layer within a semiconductor integrated circuit having a plurality of stacked layers and a pattern of another layer;
    categorizing the length measurement results of the length measurement points into at least groups for the pattern of one layer and for the pattern of another layer; and performing a statistical processing of the length measurement results of the length measurement points at the different positions to evaluate the length measurement results for each of the categorized groups of the length measurement results.

5. The pattern length measurement method according to claim 4, wherein the statistical processing includes an average value calculation of the length measurement results.

6. The pattern length measurement method according to claim 4, further comprising:
determining an allowable error value of length measurement result with respect to each length measurement result group categorized.

7. A computer program product, including a non-transitory computer readable medium, for controlling a computer operative to measure a length between an edge of a pattern to be extracted from an image obtained by a scanning electron microscope and a contour corresponding to an (other) edge on the design data of the pattern, the computer program product being programmed to execute a sequence of functions comprising:
acquiring an image of a region containing the pattern;
measuring a length of length measurement points at different positions between an edge of the pattern and the contour;
categorizing length measurement results of the length measurement points into predetermined region units; and
performing a statistical processing of the length measurement results of the length measurement points at the different positions for each of the categorized region units to calculate the length measurement results for each of the categorized region units.

8. The computer program product according to claim 7, wherein said categorizing is performed between a bent part of the pattern and a linear part thereof.

9. The computer program product according to claim 7, wherein said categorizing is performed between a part at which a proximity correction effect pattern is formed and a remaining part.

10. The computer program product according to claim 7, wherein said categorizing is done between a region with more than two patterns overlapping together therein and a remaining region.

11. The computer program product according to claim 10, wherein said categorizing is done between a place for forming therein a transistor region with a plurality of overlapping patterns and a remaining place.

12. A length measurement apparatus, comprising a calculating device for measuring a length between an edge of a pattern extracted from an image data obtained from a scanning electron microscope and an outline corresponding to a contour obtained based on a design data of the pattern, wherein the calculating device is configured to:
acquire the image data of a region containing the pattern,
measure a length of length measurement points at different positions between the edge of the pattern extracted from the image data and the contour corresponding to an (other) edge obtained based on the design data,
categorize length measurement results of the length measurement points into predetermined region units, and
perform a statistical processing of the length measurement results of the length measurement points at the different positions for each of the categorized region units of the length measurement results.

13. The length measurement apparatus according to claim 12, wherein the calculating device categorizes the length measurement results between a bent part of the pattern, and a linear part thereof.

14. The length measurement apparatus according to claim 12, wherein the calculating device categorizes the length measurement results between a part at which a proximity correction effect pattern is formed, and a remaining part.

15. The length measurement apparatus according to claim 12, wherein the calculating device categorizes the length measurement results between a region with more than two patterns overlapping together therein, and a remaining region.

16. The length measurement apparatus according to claim 12, wherein the calculating device categorizes the length measurement results between a place for forming therein a transistor region with a plurality of overlapping patterns, and a remaining place.

17. The length measurement apparatus according to claim 12, wherein the calculating device categorizes the length measurement results based on information on a semiconductor obtained from the design data.

18. The length measurement apparatus according to claim 12, wherein the statistical processing includes an average value calculation of the length measurement results.

* * * * *